(12) United States Patent
Zhang et al.

(10) Patent No.: US 7,994,162 B2
(45) Date of Patent: Aug. 9, 2011

(54) 2-ALKOXY-3,4,5-TRIHYDROXY-ALKYLAMIDE-BENZAZEPINES, THE PREPARATION AND USE THEREOF, AND COMPOSITIONS CONTAINING THE SAME

(75) Inventors: Jidong Zhang, Paris (FR); Frederico Nardi, Paris (FR); Alain Commerçon, Vitry-sur-Seine (FR)

(73) Assignee: Sanofi-Aventis, Paris (FR)

( * ) Notice: Subject to any disclaimer, the term of this patent is extended or adjusted under 35 U.S.C. 154(b) by 276 days.

(21) Appl. No.: 12/267,689

(22) Filed: Nov. 10, 2008

(65) Prior Publication Data

US 2009/0099152 A1    Apr. 16, 2009

Related U.S. Application Data

(63) Continuation of application No. PCT/FR2007/000866, filed on May 23, 2007.

(30) Foreign Application Priority Data

May 24, 2006  (FR) ..................... 06 04733

(51) Int. Cl.
C07D 487/00    (2006.01)
C07D 491/00    (2006.01)
C07D 307/78    (2006.01)
A61K 31/55     (2006.01)

(52) U.S. Cl. .................. 514/212.07; 540/523; 549/305; 549/306

(58) Field of Classification Search ............ 540/523; 549/305, 306; 514/212.07
See application file for complete search history.

(56) References Cited

U.S. PATENT DOCUMENTS

| | | | |
|---|---|---|---|
| 4,692,522 A | 9/1987 | Parsons et al. | |
| 4,831,135 A | 5/1989 | Crews et al. | |
| 5,283,241 A | 2/1994 | Bochis et al. | |
| 6,239,127 B1 | 5/2001 | Kinder, Jr. et al. | |
| 7,153,846 B2 | 12/2006 | Hoffmann et al. | |
| 7,550,453 B2 * | 6/2009 | Zhang et al. | 514/210.02 |
| 2002/0128474 A1 | 9/2002 | Xu et al. | |
| 2007/0065929 A1 | 3/2007 | Hoffmann et al. | |
| 2007/0065932 A1 | 3/2007 | Haag-Richter et al. | |
| 2007/0244087 A1 | 10/2007 | Zhang et al. | |
| 2007/0249584 A1 | 10/2007 | Zhang et al. | |

FOREIGN PATENT DOCUMENTS

| | | |
|---|---|---|
| EP | 0 687 673 A1 | 12/1995 |
| JP | 2004262793 | 9/2004 |
| WO | WO 98/35941 | 8/1998 |
| WO | WO 00/29382 | 5/2000 |
| WO | WO 01/85697 A1 | 11/2001 |
| WO | WO 02/39990 A2 | 5/2002 |
| WO | WO 2005/014574 A1 | 2/2005 |
| WO | WO 2005/044803 | 5/2005 |
| WO | WO 2006/056696 A2 | 6/2006 |

OTHER PUBLICATIONS

U.S. Appl. No. 12/267,691, filed Nov. 10, 2008, Zhang et al.
U.S. Appl. No. 12/267,692, filed Nov. 10, 2008, Zhang et al.
Adamczeski et al, Novel Sponge-Derived Amino Acids. 5. Structures, Stereochemistry, and Synthesis of Several New Heterocycles, J. Am. Chem. Soc. 1989, 111, pp. 647-654.
Chang et al, Synthesis of optically active alpha-aminobenzolactam via an oxidative-cyclization reaction, Tetrahedron: Asymmetry 14 (2003) pp. 2081-2085.
Groweiss, et al., Cytotoxic Metabolites from an Australian Collection of the Sponge, J. Nat. Prod.; 1999; 62; pp. 1691-1693.
Kinder et al, Synthesis and Antitumor Activity of Ester-Modified Analogues of Bengamide B, J. Med. Chem. 2001, 44, pp. 3692-3699.
Morton et al, Novel Solid-Phase Sythesis of 1,5-benzothiazepine-4-one Derivatives, Tetrahedron Letters 41 (2000) pp. 3029-3033.
Parsons et al, Cholecystokinin Antagonists. Synthesis and Biological Evaluation of a 3-Substituted Benzolactams, J. Med. Chem. 1989, 32, pp. 1681-1685.
Quinoa et al, Bengamides, Heterocyclic Anthelminthics from a Jaspidae Marine Sponge, J. Org. Chem. (1986) 51, pp. 4494-4497.
Ramana et al, A Carbohydrate-Based Approach for the Total Synthesis of 1,3-Polyol/alpha-Pyrone Antifungal Natural Products, J. Org. Chem. 2005, 70, pp. 8216-8219.
Slade et al, Angiotensin Converting Enzyme Inhibitors: 1,5-Benzothiazepine Derivatives, J. Med. Chem., 1985, 28, pp. 1517-1521.
Thale et al, Bengamides Revisited: New Structures and Antitumor Studies, J. Org. Chem. 2001, 66, pp. 1733-1741.

* cited by examiner

*Primary Examiner* — Bruck Kifle
(74) *Attorney, Agent, or Firm* — Scully, Scott, Murphy & Presser, P.C.

(57) ABSTRACT

The present invention relates to 2-alkoxy-3,4,5-trihydroxy-alkylamide benzodiazepine compounds, to pharmaceutical compositions comprising such compounds, to methods of treatment comprising administering such compounds, to processes for the preparation of such compounds, and to intermediate precursors to such compounds.

29 Claims, No Drawings

2-ALKOXY-3,4,5-TRIHYDROXY-ALKYLAMIDE-BENZAZEPINES, THE PREPARATION AND USE THEREOF, AND COMPOSITIONS CONTAINING THE SAME

The present invention relates in particular to 2-alkoxy-3,4,5-trihydroxy-alkylamide-benzazepines, to the preparation thereof, to compositions containing them, and to the use thereof as a medicament.

More particularly, and according to a first aspect, the invention relates to 2-alkoxy-3,4,5-trihydroxy-alkylamide-benzazepines that can be used as anticancer agents.

2-Methoxy-3,4,5-trihydroxyalkylamides have been described in U.S. Pat. No. 6,239,127, US 20010044433 A1, WO 01/85697, WO 00/29382, U.S. Pat. No. 4,831,135, EP687673 and US 20020128474 A1. These documents essentially disclose bengamide analogues and derivatives, bengamide being a natural product isolated from a marine sponge, *Jaspis coriacea*.

These same products have been described in the literature: J. Org. Chem. (1986), 51(23), 4494-7; J. Org. Chem. (2001), 66(5), 1733-41; J. Med. Chem. 2001, 44, 3692-9.

The problem that the present invention is intended to solve is that of obtaining new products with anticancer activity. In addition to maintaining an anticancer activity, some of these new products may also have advantageous properties in relation to their pharmacological activity, such as their pharmacokinetics, bioavailability, solubility, stability, toxicity, absorption or metabolism.

A subject of the present invention is the products corresponding to the following formula (I):

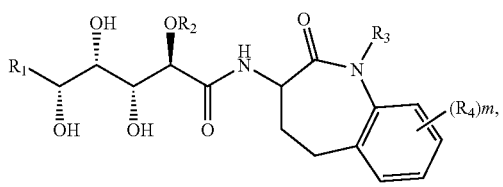

in which:
a) $R_1$ is independently selected from the group consisting of $(C_1-C_{12})$alkyl, $(C_2-C_{12})$alkenyl, $(C_2-C_{12})$alkynyl, cycloalkyl, heterocyclyl, aryl, heteroaryl, cycloalkyl$(C_1-C_{12})$alkyl, cycloalkyl$(C_2-C_{12})$alkenyl, cycloalkyl$(C_2-C_{12})$alkynyl, heterocyclyl$(C_1-C_{12})$alkyl, heterocyclyl$(C_2-C_{12})$alkenyl, heterocyclyl$(C_2-C_{12})$alkynyl, aryl$(C_1-C_{12})$alkyl, aryl$(C_2-C_{12})$alkenyl, aryl$(C_2-C_{12})$alkynyl, heteroaryl$(C_1-C_{12})$alkyl, heteroaryl$(C_2-C_{12})$alkenyl, heteroaryl$(C_2-C_{12})$alkynyl, the aryl group of each $R_1$, being optionally substituted with one or more halogens;
b) $R_2$ is selected from the group consisting of $(C_1-C_6)$alkyl, aryl$(C_1-C_6)$alkyl, heteroaryl$(C_1-C_6)$alkyl, aryl, heteroaryl, $(C_1-C_6)$alkylthio$(C_1-C_6)$alkyl, di$(C_1-C_6)$alkylamino$(C_1-C_6)$alkyl, aryloxy$(C_1-C_6)$alkyl, $(C_1-C_6)$alkoxy$(C_1-C_6)$alkyl;
c) $R_3$ is selected from the group consisting of H, COO($R_5$), CONH($R_5$), CO($R_5$), O($R_5$) and $R_5$;
d) $R_4$ is independently selected from the group consisting of F, Cl, Br, N($R_5$)$_2$, NO$_2$, CN, COO($R_5$), CON($R_5$)$_2$, NHCO($R_5$), NHCOO($R_5$), OCONH($R_5$), O($R_5$) and $R_5$, or else two substituents $R_4$, attached to 2 adjacent carbons of the phenyl, together form a ring selected from a cycloalkyl, heterocyclyl, aryl or heteroaryl, optionally substituted with one or more $R_4$;
e) m has the value 0, 1, 2, 3 or 4;
f) $R_5$ is independently selected from a doublet of nonbonding electrons, H, $(C_1-C_{12})$alkyl, $(C_2-C_{12})$alkenyl, $(C_2-C_{12})$alkynyl, halo$(C_1-C_{12})$alkyl, aryl$(C_1-C_{12})$alkyl, heteroaryl$(C_1-C_{12})$alkyl, heteroarylaryl$(C_1-C_{12})$alkyl, aryl, heteroaryl and cycloalkyl, in which each $R_5$ is optionally substituted with at least one substituent selected from OH, halogen, $(C_1-C_4)$alkyl, $(C_1-C_4)$alkoxy, aryl$(C_1-C_4)$alkyl, aryl, heteroaryl$(C_1-C_4)$alkyl, heteroaryl, —N(CH$_3$)$_2$, —NH$_2$, CONH$_2$,

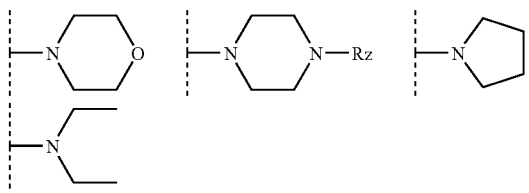

each of the Rz is independently selected from the group consisting of H, COO($R_5$), CONH($R_5$), CON($R_5$)$_2$, CO($R_5$) and $R_5$, in which each $R_5$ is independently selected from $(C_1-C_4)$alkyl, halo$(C_1-C_4)$alkyl, aryl$(C_1-C_4)$alkyl and heteroaryl$(C_1-C_4)$alkyl, in which each $R_5$ is optionally substituted with a substituent selected from OH, halogen, $(C_1-C_4)$alkyl, $(C_1-C_4)$alkoxy, aryl$(C_1-C_4)$alkyl, aryl, heteroaryl$(C_1-C_4)$alkyl and heteroaryl;

with the proviso that, when $R_1$ is (E)-CH=CH—C(CH$_3$)$_3$, $R_2$ is methyl and $R_3$ is H, then m is other than 0.

A subject of the present invention is the products of formula (I) below in which $R_1$ is independently selected from the group consisting of $(C_1-C_{12})$alkyl, $(C_2-C_{12})$alkenyl, $(C_2-C_{12})$alkynyl, cycloalkyl, heterocyclyl, aryl, heteroaryl, aryl$(C_1-C_{12})$alkyl, aryl$(C_2-C_{12})$alkenyl, aryl$(C_2-C_{12})$alkynyl, heteroaryl$(C_1-C_{12})$alkyl, heteroaryl$(C_2-C_{12})$alkenyl and heteroaryl$(C_2-C_{12})$alkynyl.

A subject of the present invention is the products of formula (I) below in which $R_2$ is selected from the group consisting of $(C_1-C_6)$alkyl, aryl$(C_1-C_6)$alkyl, heteroaryl$(C_1-C_6)$alkyl, aryl, heteroaryl, $(C_2-C_{12})$alkenylaryl, $(C_2-C_{12})$alkenylheteroaryl, $(C_1-C_6)$alkylthio$(C_1-C_6)$alkyl, di$(C_1-C_6)$alkylamino$(C_1-C_6)$alkyl and aryloxy$(C_1-C_6)$alkyl.

According to the invention, $R_1$ is preferably selected from —C($R_6$)=C($R_7$)($R_8$) in which $R_6$, $R_7$, are $R_8$ are independently selected from H, $(C_1-C_6)$alkyl, cycloalkyl, heterocyclyl, aryl and heteroaryl.

More preferably, $R_1$ is selected from (E)-CH=CH—CH(CH$_3$)(C$_2$H$_5$), (E)CH=CH—CH(CH$_3$)$_2$ and (E)-CH=CH—C(CH$_3$)$_3$, or else from (E)-C(CH$_3$)=CH—CH(CH$_3$)(C$_2$H$_5$), (E)-C(CH$_3$)=CH—CH(CH$_3$)$_2$ and (E)-C(CH$_3$)=CH—C(CH$_3$)$_3$.

More preferably, $R_1$ is selected from (E)-CH=CH—C$_5$H$_9$.

According to the invention, $R_2$ is preferably methyl.

Among the subjects of the present invention, a first group is characterized in that $R_3$ is independently selected from: a methyl group or a (3,5-difluorophenyl)methyl group. A second group is characterized in that $R_3$ is H.

Among the subjects of the present invention, a third group is characterized in that $R_4$ is independently selected from: F, Cl, Br, phenyl and pyridinyl. A fourth group is characterized in that m is 0.

Preferably, the invention relates to the products exemplified in Table 1.

According to another aspect, the invention relates to the processes for preparing the products of formula (I) or (I'). The products of formula (I') are optionally active precursors of the products of formula (I). The products of formula (I) are obtained from the products of formula (I') by means of processes that have been described or by means of one or more reactions that are conventional for those skilled in the art, for instance a cyclopropanation, an oxidation or a chiral separation.

The products of formula (I) or (I') can be obtained by hydrolysis of a product of formula (II):

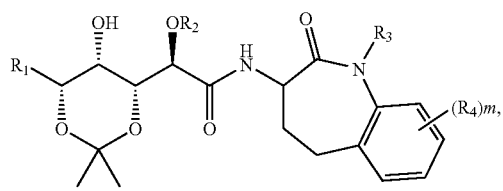

(II)

in which $R_1$, $R_2$, $R_3$, $R_4$ and m are as defined above.

The products of formula (II) can be obtained by reaction of a product of formula (III):

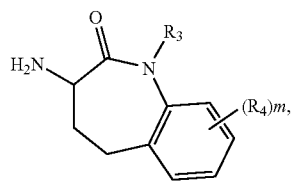

(III)

in which $R_3$, $R_4$ and m are as defined above, with a product of formula (IV):

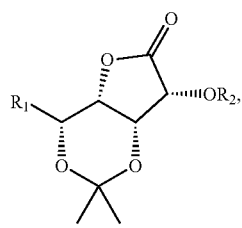

(IV)

in which $R_1$ and $R_2$ are as defined above.

The products of formula (I) or (I') can also be obtained by reaction of a product of formula (III) as defined above, with a product of formula (V):

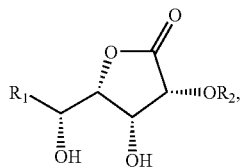

(V)

in which $R_1$ and $R_2$ are as defined above.

The products of formula (V) can be obtained by hydrolysis of a product of formula (IV):

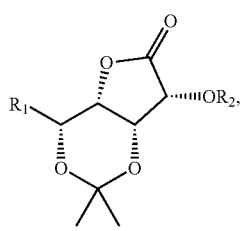

(IV)

in which $R_1$ and $R_2$ are as defined above. Products of formula (V) for which $R_1$ is —CH═CH—R'$_1$ can also be obtained by hydrolysis of a product of formula (VII):

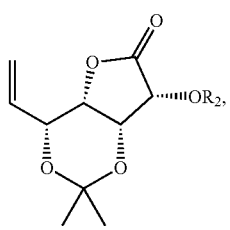

(VII)

in which $R_2$ is as defined above, in order to obtain a product of formula (VI):

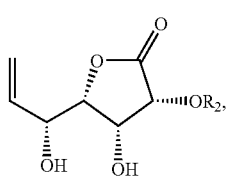

(VI)

in which $R_2$ is as defined above, which is subjected to a metathesis in order to obtain a product of formula (V):

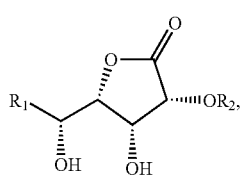

(V)

for which $R_1$ is —CH═CH—R'$_1$ and R'$_1$ is a $(C_1$-$C_6)$alkyl, cycloalkyl, heterocyclyl, aryl or heteroaryl group.

The products of formula (VII) can be obtained by double dehydration of a product of formula (VIII):

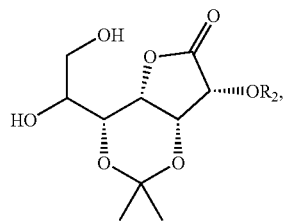

(VIII)

in which $R_2$ is as defined above.

The products of formulae (I') and (II) as defined above, with the exception of those for which $R_1$ is (E)-CH=CH—C(CH$_3$)$_3$, $R_2$ is methyl, $R_3$ is H and m is 0, are a subject of the present invention.

The products of formula (III) for which $R_3$ is H, methyl or (3,5-difluorophenyl)-methyl and $R_4$ is a bromine atom or a phenyl or else m has the value 0, with the exception of those for which $R_3$ is H and m has the value 0, are a subject of the present invention.

The products of formulae (IV) and (V) for which $R_2$ is methyl and $R_1$ is -(E)-CH=CH—C$_5$H$_9$, are a subject of the present invention.

The products of formula (VI) for which $R_2$ is methyl, are a subject of the present invention. The products of formula (VII) for which $R_2$ is methyl, are a subject of the present invention.

The products according to the present invention can exist in the form of bases, of addition salts with acids, of solvates, of hydrates or of prodrugs.

The products according to the invention can be in nonchiral form or racemic form, or in a form enriched in a steroisomer or in a form enriched in an enantiomer; and can optionally be salified. The products for which the carbon attached to the exocyclic amine is in the (S) configuration are preferred.

A product in accordance with the invention may be used for the manufacture of a medicament that can be used for preventing or treating a pathological condition, in particular a cancer.

The products of the present invention can also be used for the manufacture of a medicament that can be used for preventing or treating a pathological condition in which neovascularization or angiogenesis takes place in an inappropriate manner, i.e. in cancers in general, and in specific cancers such as Kaposi's sarcoma or infantile haemangioma, but also in rheumatoid arthritis, osteoarthritis and/or related pain, inflammatory bowel diseases such as ulcerative colitis or Crohn's disease, eye pathologies such as age-related macular degeneration or diabetic retinopathies, chronic inflammation and psoriasis.

Angiogenesis is a process for generating new blood capillaries from pre-existing vessels. Tumour angiogenesis (formation of new blood vessels), which is essential to tumour growth, is also one of the essential factors of metastatic dissemination (Oncogene. 2003 May 19; 22(20):3172-9; Nat. Med. 1995 January; 1(1):27-31).

The present invention also relates to the therapeutic compositions containing a compound according to the invention, in combination with an excipient that is pharmaceutically acceptable according to the chosen method of administration. The pharmaceutical composition may be in solid or liquid form or in the form of liposomes.

Among the solid compositions, mention may be made of powders, gelatin capsules and tablets. Among the oral forms, solid forms protected against the acidic medium of the stomach may also be included. The supports used for the solid forms consist in particular of mineral supports such as phosphates or carbonates, or organic supports such as lactose, celluloses, starch or polymers. The liquid forms consist of solutions, suspensions or dispersions. They contain, as dispersive support, either water or an organic solvent (ethanol, NMP or the like) or mixtures of surfactants and solvents or of complexing agents and solvents.

The liquid forms will preferably be injectable and, as a result, will have a formulation that is acceptable for such a use.

Acceptable routes of administration by injection include intravenous, intraperitoneal, intramuscular and subcutaneous routes, the intravenous route being preferred.

The administered dose of the compounds of the invention will be adapted by the practitioner according to the route of administration to the patient and the condition of said patient.

The compounds of the present invention can be administered alone or as a mixture with other anticancer agents. Among the possible combinations, mention may be made of:

alkylating agents, and in particular cyclophosphamide, melphalan, ifosfamide, chlorambucil, busulphan, thiotepa, prednimustine, carmustin, lomustin, semustin, streptozotocin, decarbazine, temozolomide, procarbazine and hexamethylmelamine;

platinum derivatives, such as in particular cisplatin, carboplatin or oxaliplatin;

antibiotics, such as in particular bleomycin, mitomycin or dactinomycin;

antimicrotubule agents, such as in particular vinblastine, vincristine, vindesine, vinorelbine or taxoids (paclitaxel and docetaxel);

anthracyclines, such as in particular doxorubicin, daunorubicin, idarubicin, epirubicin, mitoxantrone or losoxantrone;

topoisomerases of groups I and II, such as etoposide, teniposide, amsacrine, irinotecan, topotecan and tomudex;

fluoropyrimidines such as 5-fluorouracil, UFT or floxuridine;

cytidine analogues such as 5-azacytidine, cytarabine, gemcitabine, 6-mercaptopurine or 6-thioguanine;

adenosine analogues such as pentostatin, cytarabine or fludarabine phosphate;

methotrexate and folinic acid;

various enzymes and compounds such as L-asparaginase, hydroxyurea, trans-retinoic acid, suramine, dexrazoxane, amifostine, herceptin and also oestrogenic and androgenic hormones;

antivascular agents, such as combretastatin derivatives for example CA4P, chalcones or colchicine, for example ZD6126, and prodrugs thereof;

kinase inhibitors such as ertonilib or imatinib;

biotherapeutic agents, for instance antibodies, such as rituximab, bevacizumab, cetuximab, trastuzumab or alemtuzumab;

proteasome inhibitors such as bortesomib.

It is also possible to combine the compounds of the present invention with a radiation treatment. These treatments can be administered simultaneously, separately or sequentially. The treatment will be adapted by the practitioner according to the patient to be treated.

DEFINITIONS

The term "halogen" refers to an element selected from F, Cl, Br and I.

The term "alkyl" refers to a linear or branched, saturated hydrocarbon-based substituent containing from 1 to 12 carbon atoms. Methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 1,1- dimethylpropyl, 1,2-dimethylpropyl, 2,2-dimethylpropyl, 1-ethylpropyl, hexyl, 1-methylpentyl, 2-methylpentyl, 1-ethylbutyl, 2-ethylbutyl, 3,3-dimethylbutyl, heptyl, 1-ethylpentyl, octyl, nonyl, decyl, undecyl and dodecyl substituents are examples of an alkyl substituent.

The term "alkenyl" refers to a linear or branched hydrocarbon-based substituent having one or more unsaturations, containing from 2 to 12 carbon atoms. Ethylenyl, 1-methylethylenyl, prop-1-enyl, prop-2-enyl, Z-1-methylprop-1-enyl, E-1-methylprop-1-enyl, Z-1,2-dimethylprop-1-enyl, E-1,2-dimethylprop-1-enyl, but-1,3-dienyl, 1-methyl idenylprop-2-enyl, Z-2-methyl but-1,3-dienyl, E-2-methylbut-1,3-dienyl, 2-methyl-1-methylidenylprop-2-enyl, undec-1-enyl and undec-10-enyl substituents are examples of an alkylene substituent.

The term "alkynyl" refers to a linear or branched hydrocarbon-based substituent having at least two unsaturations, borne by a pair of vicinal carbon atoms, and containing from 2 to 12 carbon atoms. Ethynyl, prop-1-ynyl, prop-2-ynyl and but-1-ynyl substituents are examples of an alkynyl substituent.

The term "aryl" refers to a monocyclic or polycyclic aromatic substituent containing from 6 to 14 carbon atoms. Phenyl, naphth-1-yl, naphth-2-yl, anthracen-9-yl, 1,2,3,4-tetrahydronaphth-5-yl and 1,2,3,4-tetrahydronaphth-6-yl substituents are examples of an aryl substituent.

The term "heteroaryl" refers to a monocyclic or polycyclic heteroaromatic substituent containing from 1 to 13 carbon atoms and from 1 to 4 heteroatoms. Pyrrol-1-yl; pyrrol-2-yl; pyrrol-3-yl; furyl; thienyl; imidazolyl; oxazolyl; thiazolyl; isoxazolyl; isothiazolyl; 1,2,4-triazolyl; oxadiazolyl; thiadiazolyl; tetrazolyl; pyridyl; pyrimidyl; pyrazinyl; 1,3,5-triazinyl; indolyl; benzo[b]furyl; benzo[b]thienyl; indazolyl; benzimidazolyl; azaindolyl; quinoleyl; isoquinoleyl; carbazolyl and acridyl substituents are examples of a heteroaryl substituent.

The term "heteroatom" refers herein to an atom, that is at least divalent, other than carbon. N; 0; S and Se are examples of a heteroatom.

The term "cycloalkyl" refers to a saturated or partially unsaturated cyclic hydrocarbon-based substituent containing from 3 to 12 carbon atoms. Cyclopropyl, cyclobutyl, cyclopentyl, cyclopentenyl, cyclopentadienyl, cyclohexyl, cyclohexenyl, cycloheptyl, bicyclo[2.2.1]heptyl, cyclooctyl, bicyclo[2.2.2]octyl, adamantyl and perhydronaphthyl substituents are examples of a cycloalkyl substituent.

The term "heterocyclyl" refers to a saturated or partially unsaturated, cyclic hydrocarbon-based substituent containing from 1 to 13 carbon atoms and from 1 to 4 heteroatoms. Preferably, the saturated or partially unsaturated, cyclic hydrocarbon-based substituent will be monocyclic and will contain 4 or 5 carbon atoms and 1 to 3 heteroatoms.

As regards the term "condensed phenyl", when m has the value zero, it is intended to mean that it is an unsubstituted phenyl (or substituted with 4 hydrogen atoms), and when m has the value 1, 2, 3 or 4, it is intended to mean that 1, 2, 3 or 4 hydrogen atoms are substituted with a substituent $R_4$.

The advantages of the invention will be more particularly illustrated by the following examples:

Abbreviations:

Ac acetate; Bn benzyl; ° C. degrees Celsius; cat. catalyst; TLC thin-layer chromatography; PCC preparative column chromatography; cm centimetre; δ chemical shift; d doublet; dd doublet of doublets; DMF dimethylformamide; DMSO-$d_6$ deuterated dimethyl sulphoxide; dt doublet of triplets; eq. equivalent; ES+/−electrospray (positive/negative modes); Et ethyl; g gram; h hour; Hz hertz; $IC_{50}$ constant for 50% inhibition of activity; iPr isopropyl; d day; J coupling constant; LCMS liquid chromatography coupled to mass spectrometry; m multiplet; Me methyl; mg milligram; MHz megahertz; ml millilitre; μl microlitre; mm millimetre; μm micrometre; mmol millimole; min minute; N mol·L$^{-1}$; Mp melting point; Ph phenyl; ppm parts per million; q quadruplet; YId yield; Rf frontal ratios; $^1$H NMR proton nuclear magnetic resonance; s singlet; bs broad singlet; t triplet; AT ambient temperature; tBu tert-butyl; TFA trifluoroacetic acid; THF tetrahydrofuran; $t_R$ retention time; U.V. ultraviolet; V volt.

EX1

N-[1-(3,5-difluorobenzyl)-2-oxo-2,3,4,5-tetrahydro-1H-1-benzazepin-3-yl]-((E)-(2R,3R,4S,5R)-3,4,5-trihydroxy-2-methoxy-8,8-dimethylnon-6-enamide

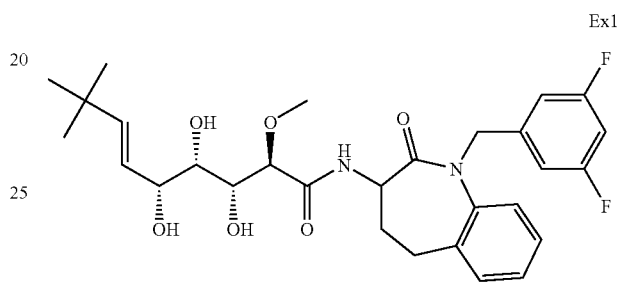

Step 1: Preparation of tert-butyl (2-oxo-2,3,4,5-tetrahydro-1H-1-benzazepin-3-yl)carbamate (2)

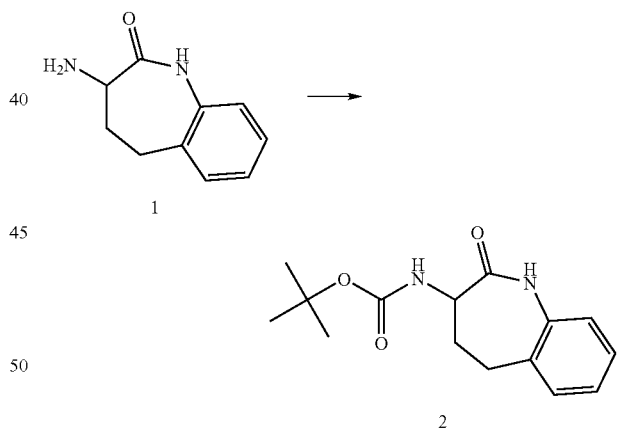

A solution of 2.48 g of tBoc$_2$O (11.4 mmol) in 50 ml of CHCl$_3$ is added, at 0° C., to a 250 ml round-bottomed flask containing 2.0 g of 1 (11.4 mmol) (3-amino-1,3,4,5,-tetrahydro-2H-1-benzazepin-2-one, commercial from Interchim), 1.15 ml of TEA (11.4 mmol) and 50 ml of CHCl$_3$. The medium is stirred for 2 h at 0° C. under argon. The reaction medium is washed with 10 ml of HCl (1N) and 100 ml of water. The organic phase is dried over MgSO$_4$, filtered and evaporated to dryness. 3.75 g of a cream solid are obtained, which solid is triturated in 20 ml of isopropyl ether. After filter-drying, 2.3 g of 2 (off-white solid) are obtained.

$^1$H NMR (400 MHz, DMSO-$d_6$), δ(ppm): 1.33 (s, 9H); 2.06 (m, 1H); 2.18 (m, 1H); from 2.60 to 2.70 (m, 2H); 3.87

(m, 1H); 6.92 (d, J=8.0 Hz, 1H); 7.00 (d, J=7.5 Hz, 1H); 7.11 (broad t, J=7.5 Hz, 1H); from 7.21 to 7.29 (m, 2H); 9.68 (s, 1H).

Step 2: Preparation of tert-butyl [1-(3,5-difluorobenzyl)-2-oxo-2,3,4,5-tetrahydro-1H-1-benzazepin-3-yl] carbamate (3)

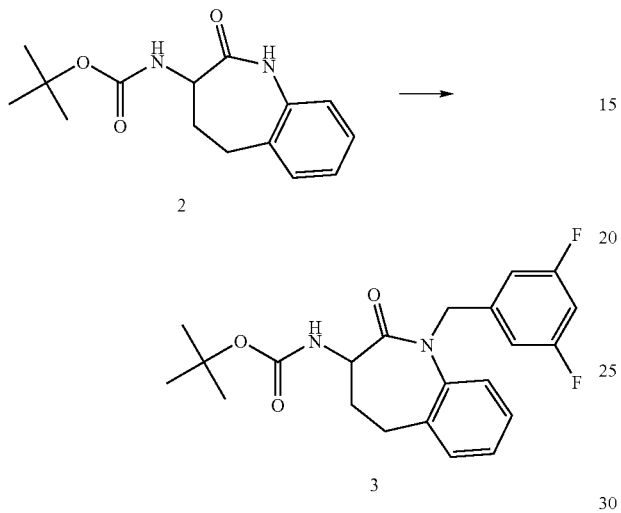

72 mg of sodium hydride in suspension at 60% in oil (1.81 mmol) are introduced, at AT, into a 100 ml round-bottomed flask, with stirring and under an argon atmosphere, containing 20 ml of THF and 0.5 g of 2 (1.81 mmol). The medium is stirred for 1 h and then 0.75 g (3.62 mmol) of 3,5-difluorobenzyl bromide is added. The medium is left stirring at AT overnight. 50 ml of EtOAc are added and the organic phase is washed with 50 ml of water. The organic phase is dried over MgSO$_4$, filtered and then evaporated to dryness. 1 g of a white solid is obtained. After trituration with 20 ml of isopropyl ether and filter-drying, 0.62 g of product 3 (white solid) is obtained.

$^1$H NMR (400 MHz, DMSO-d$_6$), δ(ppm): 1.35 (s, 9H); 2.10 (m, 2H); 2.52 (m partially masked, 1H); 2.61 (m, 1H); 3.94 (m, 1H); 4.92 (d, J=16.0 Hz, 1H); 5.10 (d, J=16.0 Hz, 1H); 6.96 (m, 2H); 7.09 (tt, J=2.5 and 9.5 Hz, 1H); from 7.17 to 7.22 (m, 3H); from 7.25 to 7.34 (m, 2H).

Step 3: Preparation of the hydrochloride of 3-amino-1-(3,5-difluorobenzyl)-1,3,4,5-tetrahydro-1-benzazepin-2-one (4)

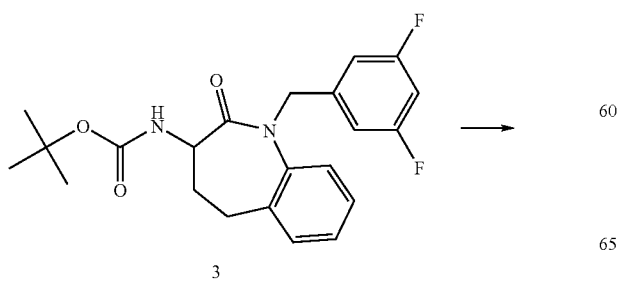

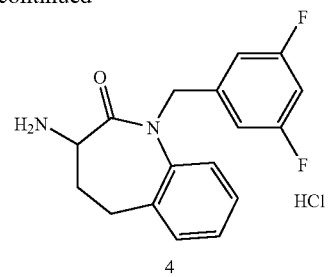

0.62 g of 3 (1.54 mmol) are taken up in a 25 ml round-bottomed flask and 10 ml of a solution of hydrochloric acid in dioxane (4M) are added. The medium is stirred for 5 h at AT under argon. After the solvent has been evaporated off, 0.46 g of amine 4 in hydrochloride form is obtained, and is used directly for the following step.

$^1$H NMR (300 MHz, DMSO-d$_6$), δ(ppm): 2.16 (m, 1H); 2.43 (m, 1H); 2.57 (m, 1H); 2.70 (m, 1H); 3.76 (dd, J=7.5 and 11.5 Hz, 1H); 5.04 (d, J=15.5 Hz, 1H); 5.12 (d, J=15.5 Hz, 1H); 6.99 (m, 2H); 7.14 (tt, J=2.5 and 9.5 Hz, 1H); from 7.22 to 7.40 (m, 4H); 8.31 (broad s, 3H).

Step 4: Preparation of N-[1-(3,5-difluorobenzyl)-2-oxo-2,3,4,5-tetrahydro-1H-1-benzazepin-3-yl]-2-[(4R,5S,6R)-6-((E)-3,3-dimethylbut-1-enyl)-5-hydroxy-2,2-dimethyl-1,3-dioxinan-4-yl]-2-methoxyacetamide (6)

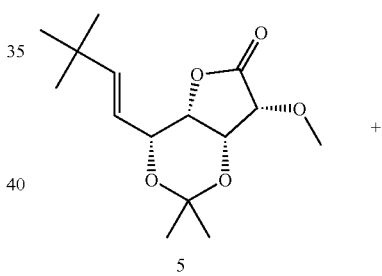

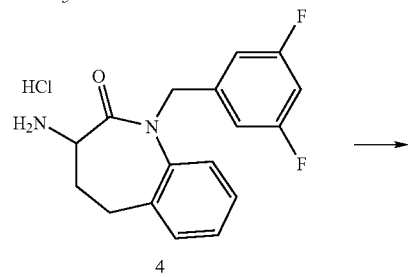

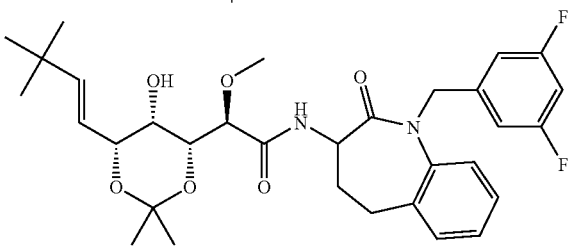

100 mg of 5 (352 μmol) (which can be prepared according to the procedures described in Org. Process Res. Dev. 2003, 7(6), 856-865), 239 mg of 4 (0.70 mmol) and 146 mg of sodium 2-ethylhexanoate (0.77 mmol) in 2 ml of THF are introduced successively into a Wheaton tube, with agitation and under an argon atmosphere. The agitation is maintained at AT for 24 h. 3 ml of ethyl acetate are added to the reaction medium. The mixture is washed successively with 3 ml of a solution of HCl (1N), then 3 ml of a saturated solution of $NaHCO_3$ and 3 ml of water. The organic phase is dried over anhydrous magnesium sulphate, filtered and then evaporated to dryness. 450 mg of a colourless oil are obtained, which oil is chromatographed on a silica cartridge (20 g, eluent $CH_2Cl_2$/MeOH—as an MeOH gradient of 1 to 10%). 122 mg of expected product 6 are recovered.

$^1$H NMR (400 MHz, DMSO-$d_6$), δ(ppm): (a 50%-50% mixture of isomers) 0.98 (s, 4.5H); 0.99 (s, 4.5H); 1.20 (s, 1.5H); 1.21 (s, 1.5H); 1.26 (s, 1.5H); 1.27 (s, 1.5H); 2.15 (m, 2H); 2.53 (m partially masked, 1H); 2.63 (m, 1H); 3.23 (s, 1.5H); 3.25 (m masked, 1H); 3.26 (s, 1.5H); 3.75 (d, J=8.5 Hz, 0.5H); 3.80 (d, J=8.5 Hz, 0.5H); 3.91 (broad d, J=8.5 Hz, 0.5H); 3.96 (broad d, J=8.5 Hz, 0.5H); from 4.20 to 4.42 (m, 3H); from 4.95 to 5.11 (m, 2H); 5.44 (resolved dd, J=7.0 and 16.0 Hz, 1H); 5.67 (resolved d, J=16.0 Hz, 1H); 6.94 (m, 2H); 7.10 (m, 1H); from 7.18 to 7.37 (m, 4H); 8.26 (d, J=8.0 Hz, 0.5H); 8.35 (d, J=7.0 Hz, 0.5H).

Step 5: Preparation of N-[1-(3,5-difluorobenzyl)-2-oxo-2,3,4,5-tetrahydro-1H-1-benzazepin-3-yl]-((E)-(2R,3R,4S,5R)-3,4,5-trihydroxy-2-methoxy-8,8-dimethylnon-6-enamide (Ex1)

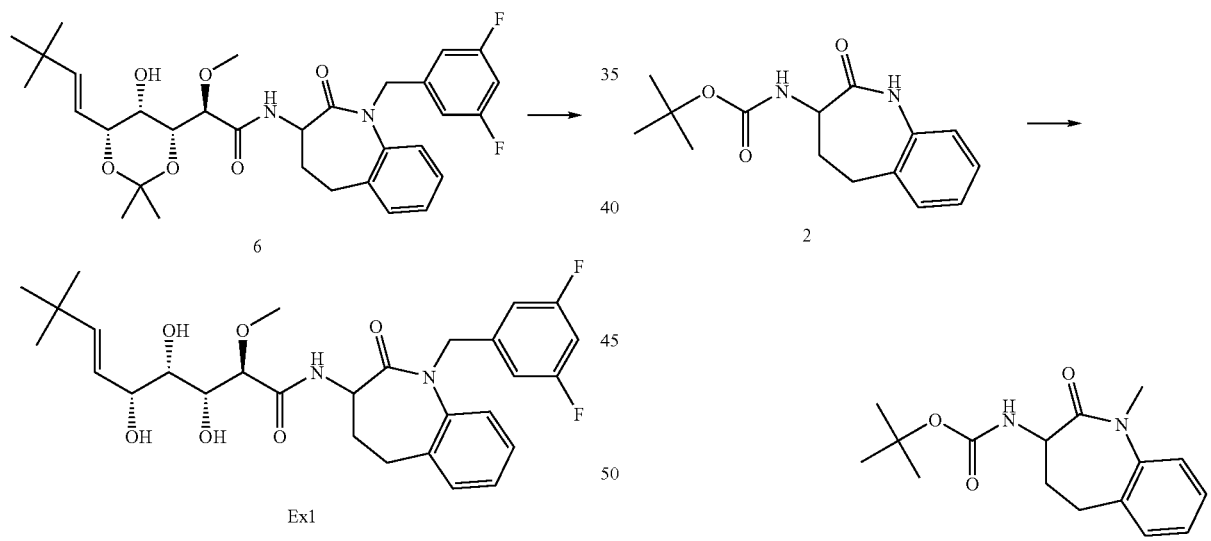

92 mg of 6 (157 μmol) in 0.8 ml of THF and 1.57 ml of 1N hydrochloric acid (1.57 mmol) are mixed in a 10 ml round-bottomed flask, with agitation and under argon. The agitation is maintained for 5 h at AT. A precipitate forms and is filter-dried over a sintered glass funnel. After washing with 0.5 ml of THF and then 2 ml of isopropyl ether and vacuum drying, 70 mg of Ex1 (white solid) are obtained.

ES: m/z=569 MNa$^+$.

$^1$H NMR (400 MHz, DMSO-$d_6$), δ(ppm): (a 50%-50% mixture of isomers) 0.94 (s, 4.5H); 0.95 (s, 4.5H); 2.18 (m, 2H); 2.53 (m partially masked, 1H); 2.63 (m, 1H); 3.22 (s, 1.5H); 3.24 (s, 1.5H); from 3.26 to 3.33 (m masked, 1H); 3.52 (m, 1H); 3.68 (d, J=8.0 Hz, 1H); 3.94 (m, 1H); from 4.18 to 4.36 (m, 3H); 4.54 (broad d, J=4.5 Hz, 1H); from 4.98 to 5.10 (m, 2H); 5.28 (resolved dd, J=7.0 and 16.0 Hz, 1H); 5.61 (d, J=16.0 Hz, 1H); 6.95 (m, 2H); 7.10 (tt, J=2.5 and 10.0 Hz, 1H); from 7.17 to 7.36 (m, 4H); 8.16 (d, J=8.0 Hz, 0.5H); 8.24 (d, J=7.0 Hz, 0.5H).

EX2

N-[1-methyl-2-oxo-2,3,4,5-tetrahydro-1H-1-benzazepin-3-yl]-((E)-(2R,3R,4S,5R)-3,4,5-trihydroxy-2-methoxy-8,8-dimethylnon-6-enamide

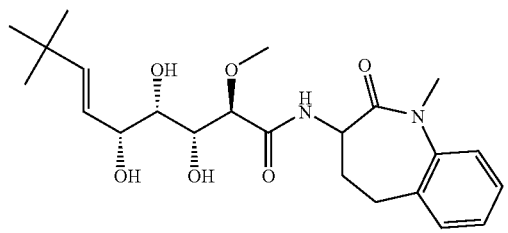

Step 1: Preparation of tert-butyl [1-methyl-2-oxo-2,3,4,5-tetrahydro-1H-1-benzazepin-3-yl]carbamate (Z)

174 mg of sodium hydride in suspension at 60% in oil (4.34 mmol) are introduced, at AT, into a 100 ml round-bottomed flask, with stirring and under an argon atmosphere, containing 50 ml of THF and 1.2 g of 2 (4.34 mmol). The medium is stirred for 1 h and then 1.23 g (8.69 mmol) of methyl iodide are added. The medium is left stirring overnight, 50 ml of EtOAc are added, and the organic phase is washed with 100 ml of water. The organic phase is dried over $MgSO_4$, filtered and then evaporated to dryness. 1.3 g of a white solid are obtained. After chromatography on a silica cartridge (40 g) (eluent $CH_2Cl_2$/MeOH—as an MeOH gradient of 1 to 10%). 0.66 g of product 7 (white solid) is obtained.

$^1$H NMR (400 MHz, DMSO-d$_6$), δ(ppm): 1.33 (s, 9H); 2.05 (m, 2H); 2.62 (m, 2H); 3.26 (s, 3H); 3.86 (m, 1H); 7.00 (d, J=8.5 Hz, 1H); 7.21 (m, 1H); 7.28 (m, 1H); 7.36 (m, 2H).

Step 2: Preparation of the hydrochloride of 3-amino-1-methyl-1,3,4,5-tetrahydro-1-benzazepin-2-one (8)

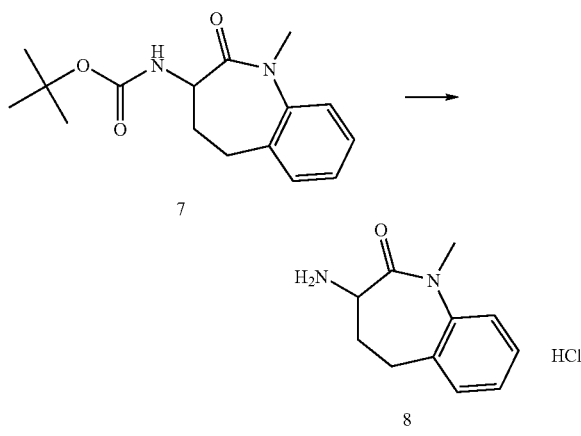

0.66 g of 7 (2.27 mmol) is taken up in a 50 ml round-bottomed flask and 15 ml of a solution of hydrochloric acid in dioxane (4M) are added. The mixture is stirred for 5 h at AT under argon. After the solvent has been evaporated off, 0.53 g of amine 8 in hydrochloride form is obtained, and is used directly for the following step.

$^1$H NMR (300 MHz, DMSO-d$_6$), δ(ppm): 2.12 (m, 1H); 2.45 (m partially masked, 1H); from 2.68 to 2.79 (m, 2H); 3.34 (s, 3H); 3.59 (dd, J=7.5 and 11.5 Hz, 1H); 7.25 (m, 1H); 7.35 (broad d, J=7.5 Hz, 1H); 7.40 (m, 2H); 8.38 (broad s, 3H).

Step 3: Preparation of (3R,4R,5S)-4-hydroxy-5-((E)-(R)-1-hydroxy-4,4-dimethylpent-2-enyl)-3-methoxy-dihydrofuran-2-one (9)

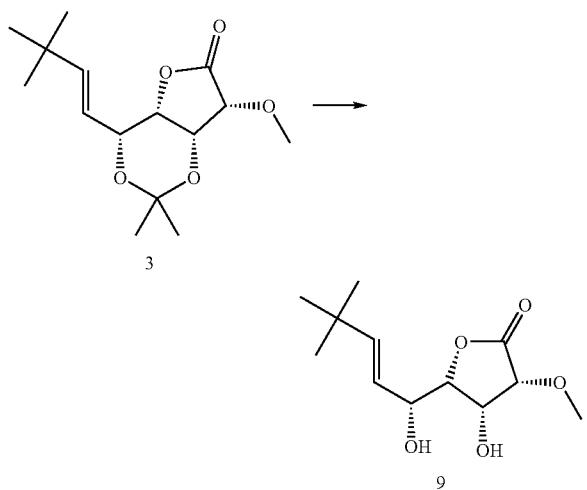

17 ml of TFA in 10 ml of water are added to a 250 ml round-bottomed flask containing 40 ml of water and 3.6 g of 3 in suspension. The medium is stirred for 1.5 h at AT. The medium is diluted with 290 ml of water, frozen and then lyophilized. 4 g of an oil are obtained, which oil is crystallized from 20 ml of isopropyl ether at AT. After filter-drying, washing with isopropyl ether and vacuum drying at 40° C., 2.46 g of expected product 7 (white crystals) are obtained.

Mp: 123° C.

IC: m/z=262 MNH$_4^+$.

$^1$H NMR (400 MHz, DMSO-d$_6$), δ(ppm): 1.00 (s, 9H); 3.41 (s, 3H); 3.93 (dd, J=2.5 and 9.0 Hz, 1H); from 4.22 to 4.31 (m, 3H); 5.19 (d, J=5.0 Hz, 1H); 5.42 (dd, J=5.0 and 16.0 Hz, 1H); 5.43 (d, J=4.5 Hz, 1H); 5.87 (d, J=16.0 Hz, 1H).

IR (KBr): 3239; 2964; 2914; 1701; 1499; 1312; 1253; 1047 & 751 cm$^{-1}$.

Step 4: Preparation of N-[1-methyl-2-oxo-2,3,4,5-tetrahydro-1H-1-benzazepin-3-yl]-((E)-(2R,3R,4S,5R)-3,4,5-trihydroxy-2-methoxy-8,8-dimethylnon-6-enamide (Ex2)

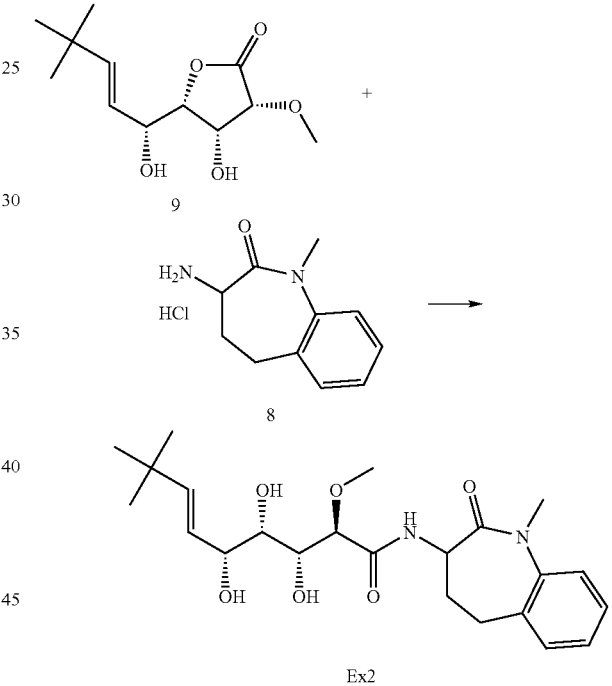

36 mg of 9 (147 μmol), 66.8 mg of 8 (0.30 mmol), 61 mg of sodium 2-ethylhexanoate (0.37 mmol) in 1.0 ml of THF are successively introduced into a Wheaton tube, with agitation and under an argon atmosphere. The agitation is maintained at AT for 24 h. The reaction medium is directly evaporated to dryness. The crude is chromatographed on a silica cartridge (5 g, eluent CH$_2$Cl$_2$/MeOH—as an MeOH gradient of 1 to 10%). 39 mg of expected product Ex2 are recovered.

ES: m/z=457 MNa$^+$; m/z=435 MH$^+$.

$^1$H NMR (400 MHz, DMSO-d$_6$), δ(ppm): (a 50%-50% mixture of isomers) 0.95 (s, 4.5H); 0.96 (s, 4.5H); 2.06 (m, 1H); 2.21 (m, 1H); from 2.60 to 2.75 (m, 2H); 3.21 (s, 3H); from 3.25 to 3.35 (m masked, 1H); 3.29 (broad s, 3H); 3.51 (broad m, 1H); 3.66 (d, J=7.5 Hz, 0.5H); 3.67 (d, J=7.5 Hz, 0.5H); 3.93 (m, 1H); 4.21 (m, 1H); from 4.28 to 4.60 (broad m, 3H); 5.28 (dd, J=7.0 and 16.0 Hz, 0.5H); 5.30 (dd, J=7.0 and 16.0 Hz, 0.5H); 5.61 (d, J=16.0 Hz, 0.5H); 5.63 (d, J=16.0

Hz, 0.5H); 7.22 (m, 1H); 7.31 (m, 1H); from 7.37 (m, 2H); 8.03 (d, J=8.0 Hz, 0.5H); 8.05 (d, J=7.0 Hz, 0.5H).

EX3

N-(7-bromo-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide and Ex3a & Ex3b Ex3

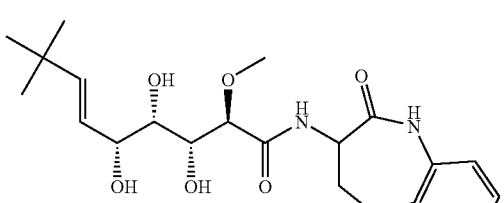

Ex3a

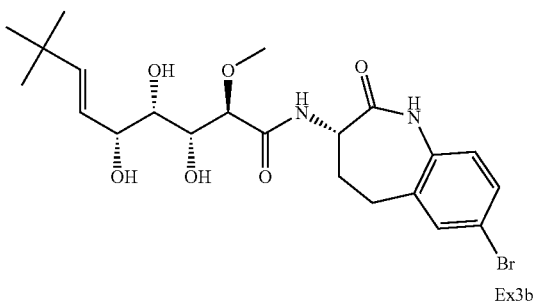

Ex3b

Step 1: Preparation of tert-butyl (7-bromo-2-oxo-2,3, 4,5-tetrahydro-1H-1-benzazepin-3-yl)carbamate (10)

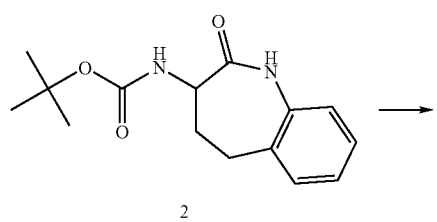

2

-continued

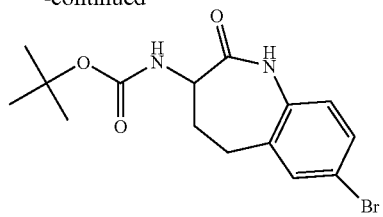

10

472 mg of N-bromosuccinimide (2.65 mmol) are introduced at AT into a 100 ml round-bottomed flask, with stirring and under an argon atmosphere, containing 40 ml of EtOAc and 0.5 g of 2 (1.8 mmol). The medium is left stirring overnight, and is washed with 40 ml of HCl (1N), 40 ml of saturated aqueous solution of NaHCO₃ and 40 ml of water. The organic phase is dried over MgSO₄, filtered and then evaporated to dryness. 1.3 g of an oil are obtained, which oil is crystallized from 10 ml of isopropyl ether. After filter-drying, 450 mg of product 10 (white solid) are obtained.

¹H NMR (400 MHz, DMSO-d₆), δ(ppm): 1.34 (s, 9H); 2.05 (m, 1H); 2.21 (m, 1H); from 2.58 to 2.72 (m, 2H); 3.86 (m, 1H); 6.95 (d, J=8.5 Hz, 1H); 6.98 (d, J=8.5 Hz, 1H); 7.44 (dd, J=2.0 and 8.5 Hz, 1H); 7.50 (d, J=2.0 Hz, 1H); 9.7 (s, 1H).

Step 2: Preparation of the hydrochloride of 3-amino-7-bromo-1,3,4,5-tetrahydro-1-benzazepin-2-one (11)

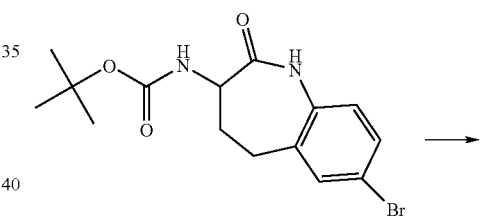

10

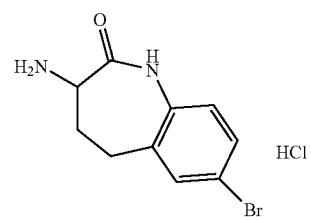

11

0.45 g of 10 (1.27 mmol) are taken up in a 25 ml round-bottomed flask and 10 ml of a solution of hydrochloric acid in dioxane (4M) are added. The medium is stirred for 5 h at AT under argon. A precipitate forms, and is filtered over a sintered glass funnel, and washed with 5 ml of dioxane and then 5 ml of isopropyl ether. 0.38 g of amine 11 in hydrochloride form is obtained.

¹H NMR (400 MHz, DMSO-d₆), δ(ppm): 2.12 (m, 1H); 2.51 (m partially masked, 1H); from 2.65 to 2.84 (m, 2H);

3.72 (dd, J=8.0 and 11.5 Hz, 1H); 6.99 (d, J=8.5 Hz, 1H); 7.48 (dd, J=2.5 and 8.5 Hz, 1H); 7.58 (d, J=2.5 Hz, 1H); 8.25 (s, 3H); 10.35 (s, 1H).

Step 3: Preparation of (R)—N-(7-bromo-2-oxo-2,3,4,5-tetrahydro-1H-1-benzazepin-3-yl)-2-[(4R,5S,6R)-6-((E)-3,3-dimethylbut-1-enyl)-5-hydroxy-2,2-dimethyl-1,3-dioxinan-4-yl]-2-methoxyacetamide (12)

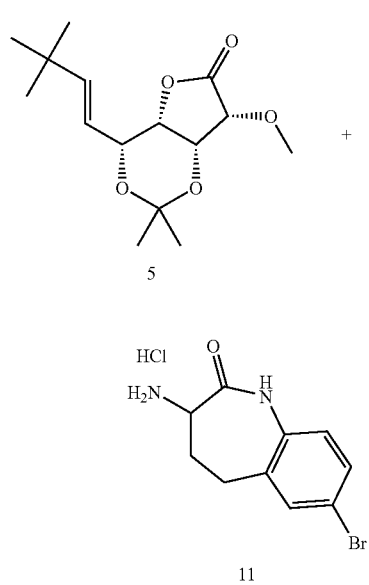

100 mg of 5 (352 μmol), 205 mg of 11 (0.70 mmol) and 146 mg of sodium 2-ethylhexanoate (0.77 mmol) in 2 ml of THF are successively introduced into a Wheaton tube, with agitation and under an argon atmosphere. The agitation is maintained at AT for 24 h. The medium is evaporated to dryness and then purified by chromatography on a silica cartridge (20 g) with an eluent of $CH_2Cl_2$/MeOH (as an MeOH gradient of 1 to 10%). 160 mg of expected product 12 are recovered.

$^1$H NMR (300 MHz, DMSO-$d_6$), δ(ppm): (a 70%-30% mixture of isomers) 0.99 (s, 9H); 1.23 (s, 0.9H); 1.25 (s, 2.1H); 1.28 (s, 0.9H); 1.29 (s, 2.1H); 2.08 (m, 1H); 2.27 (m, 1H); from 2.65 to 2.76 (m, 2H); from 3.21 to 3.34 (m masked, 1H); 3.24 (s, 2.1H); 3.26 (s, 0.9H); 3.73 (d, J=8.5 Hz, 0.7H); 3.78 (d, J=8.5 Hz, 0.3H); 3.90 (broad d, J=8.5 Hz, 0.3H); 3.96 (broad d, J=8.5 Hz, 0.7H); from 4.12 to 4.43 (m, 3H); 5.43 (dd, J=7.0 and 16.0 Hz, 0.3H); 5.44 (dd, J=7.0 and 16.0 Hz, 0.7H); 5.68 (broad d, J=16.0 Hz, 1H); 6.97 (d, J=8.5 Hz, 1H); 7.46 (dd, J=2.5 and 8.5 Hz, 1H); 7.54 (d, J=2.5 Hz, 1H); 8.08 (d, J=8.0 Hz, 0.7H); 8.15 (d, J=7.5 Hz, 0.3H); 9.85 (s, 0.3H); 9.89 (S, 0.7H).

Step 4: Preparation of N-(7-bromo-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide (Ex3) and Ex3a & Ex3b

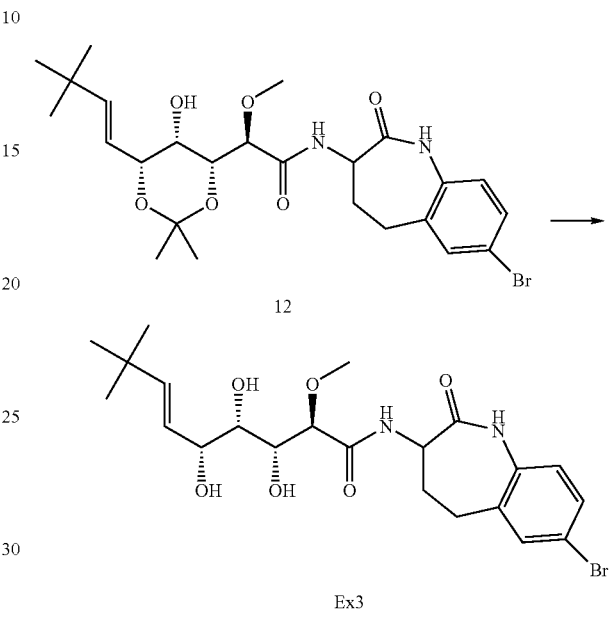

150 mg of 12 (258 μmol) in 1.4 ml of THF and 2.78 ml of 1N hydrochloric acid are introduced into a 25 ml round-bottomed flask, with agitation and under argon. The agitation is maintained for 4.5 h at AT. The medium is neutralized with NaOH (1N), to pH 7, and extracted with 2 times 3 ml of EtOAc. The combined organic phases are dried over $MgSO_4$, filtered and evaporated to dryness. The crude is chromatographed on a silica cartridge (10 g), elution being carried out with $CH_2Cl_2$/MeOH (as an MeOH gradient of 1 to 10%). 65 mg of expected product Ex3 are recovered. 40 mg of Ex3 are separated by preparative chiral HPLC (Chirapad AD-H 5 μm 250×4.6 mm, flow rate 1 ml/min, mobile phase: 50% heptane-50% EtOH, 0.1% TEA), to give 9 mg of Ex3a (tr=7.48 min) and 20 mg of Ex3b (tr=9.71 min).

ES: m/z=497 (M–H)$^-$.

Ex3: $^1$H NMR (400 MHz, DMSO-$d_6$), δ(ppm): (a 70%-30% mixture of isomers) 0.95 (s, 6.3H); 0.96 (s, 2.7H); 2.09 (m, 1H); 2.31 (m, 1H); from 2.65 to 2.73 (m, 2H); from 3.19 to 3.33 (m masked, 1H); 3.22 (s, 2.1H); 3.29 (s, 0.9H); 3.52 (m, 1H); 3.66 (d, J=8.0 Hz, 0.3H); 3.68 (d, J=7.5 Hz, 0.7H); 3.94 (m, 1H); from 4.16 to 4.41 (m, 3H); 4.55 (d, J=4.5 Hz, 1H); 5.28 (dd, J=7.0 and 16.0 Hz, 0.3H); 5.30 (dd, J=7.0 and 16.0 Hz, 0.7H); 5.61 (d, J=16.0 Hz, 0.3H); 5.63 (d, J=16.0 Hz, 0.7H); 6.97 (d, J=8.5 Hz, 1H); 7.46 (dd, J=2.5 and 8.5 Hz, 1H); 7.54 (d, J=2.5 Hz, 1H); 8.04 (d, J=7.5 Hz, 1H); 9.91 (s, 0.3H); 9.95 (s, 0.7H).

Ex3a: $^1$H NMR (400 MHz, DMSO-$d_6$), δ(ppm): 0.96 (s, 9H); 2.07 (m, 1H); 2.30 (m, 1H); 2.70 (m, 2H); 3.22 (s, 3H); from 3.27 to 3.35 (m masked, 1H); 3.51 (m, 1H); 3.67 (d, J=7.5 Hz, 1H); 3.91 (m, 1H); 4.19 (m, 1H); 4.29 (m, 2H); 4.54 (d, J=4.5 Hz, 1H); 5.29 (dd, J=7.0 and 16.0 Hz, 1H); 5.62 (d, J=16.0 Hz, 1H); 6.97 (d, J=8.5 Hz, 1H); 7.45 (dd, J=2.5 and 8.5 Hz, 1H); 7.54 (d, J=2.5 Hz, 1H); 8.02 (d, J=7.5 Hz, 1H); 9.90 (s, 1H).

EX4

N-(7-phenyl-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide and Ex4a & Ex4b

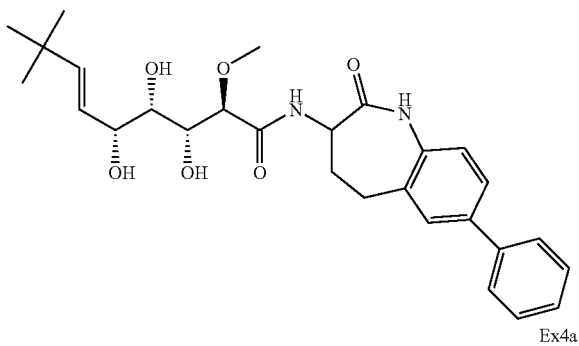

Ex4

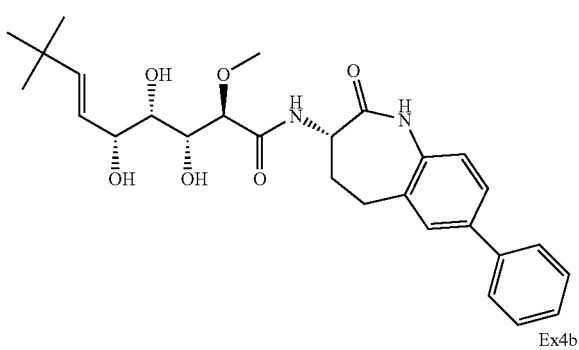

Ex4a

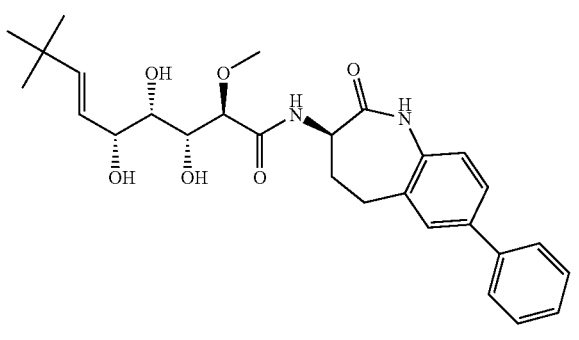

Ex4b

Step 1: Preparation of tert-butyl (7-phenyl-2-oxo-2,3,4,5-tetrahydro-1H-1-benzazepin-3-yl)carbamate (13)

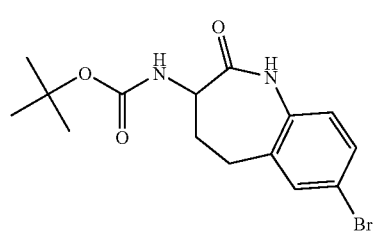

10

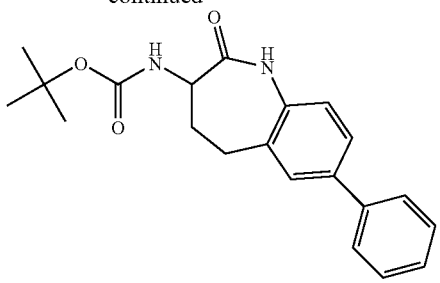

13

371 mg of phenylboronic acid (3.04 mmol), 62 mg of 1,1'-bis(diphenylphosphino)ferrocene palladium chloride ($C_{35}H_{30}Cl_4FeP_2Pd$, Mw 816.65, 0.025 mmol) and 3.96 g of caesium carbonate (12.16 mmol) are introduced into a 100 ml round-bottomed flask, with stirring and under an argon atmosphere, containing 22 ml of water, 6.5 ml of dioxane and 1.08 g of 10 (3.04 mmol). The medium is heated at 100° C., with stirring, for 1 h. The medium is filtered over celite and washed with 10 ml of dioxane, 10 ml of $CH_2Cl_2$ and 10 ml of MeOH. The filtrate is concentrated under vacuum. 25 ml of EtOAc are then added and the mixture is washed with 2 times 25 ml of water. The organic phase is dried over $MgSO_4$, filtered and evaporated to dryness. The crude is chromatographed on a silica cartridge (50 g), elution being carried out with $CH_2Cl_2$/MeOH (as an MeOH gradient: 1 to 10%). 350 mg of expected product 13 (white solid) are recovered.

$^1$H NMR (300 MHz, DMSO-$d_6$), δ(ppm): 1.34 (s, 9H); 2.09 (m, 1H); 2.25 (m, 1H); from 2.63 to 2.79 (m, 2H); 3.94 (m, 1H); 6.97 (d, J=8.5 Hz, 1H); 7.09 (d, J=8.5 Hz, 1H); 7.34 (t, J=7.5 Hz, 1H); 7.46 (t, J=7.5 Hz, 2H); 7.56 (dd, J=2.0 and 8.5 Hz, 1H); 7.58 (broad s, 1H); 7.66 (d, J=7.5 Hz, 2H); 9.77 (s, 1H).

Step 2: Preparation of the hydrochloride of 3-amino-7-phenyl-1,3,4,5-tetrahydro-1-benzazapin-2-one (14)

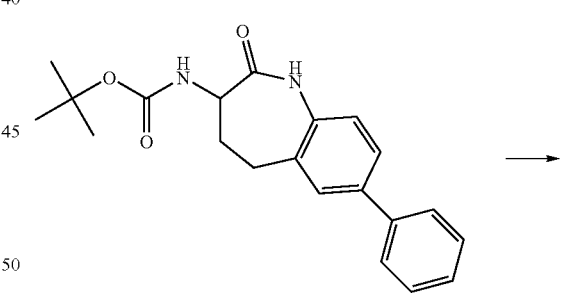

13

14

0.35 g of 13 (0.99 mmol) is taken up in a 20 ml round-bottomed flask and 5 ml of a solution of hydrochloric acid in dioxane (4M) are added. The medium is stirred for 5 h at AT under argon. A precipitate forms and is filter-dried and washed with 5 ml of dioxane and then 5 ml of isopropyl ether. After drying, 0.23 g of amine 14 in hydrochloride form is obtained.

$^1$H NMR (400 MHz, DMSO-d$_6$), δ(ppm): 2.18 (m, 1H); 2.55 (m partially masked, 1H); from 2.74 to 2.90 (m, 2H); 3.76 (dd, J=8.5 and 12.0 Hz, 1H); 7.12 (d, J=8.0 Hz, 1H); 7.36 (t, J=7.5 Hz, 1H); 7.47 (t, J=7.5 Hz, 2H); 7.60 (dd, J=2.0 and 8.0 Hz, 1H); from 7.64 to 7.69 (m, 3H); 8.19 (broad s, 3H); 10.35 (s, 1H).

Step 3: Preparation of (R)—N-(7-phenyl-2-oxo-2,3,4,5-tetrahydro-1H-1-benzazepin-3-yl)-2-[(4R,5S,6R)-6-((E)-3,3-dimethylbut-1-enyl)-5-hydroxy-2,2-dimethyl-1,3-dioxinan-4-yl]-2-methoxyacetamide (15)

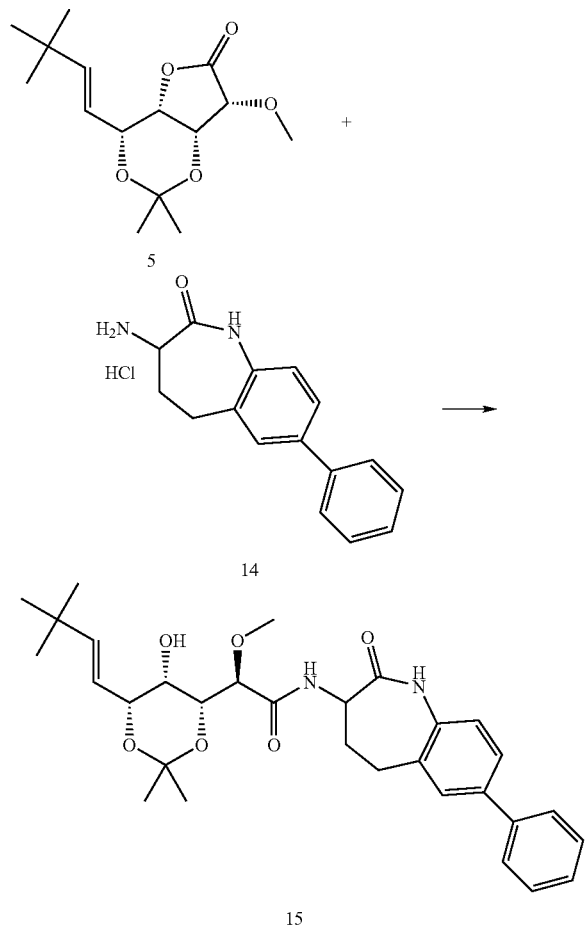

100 mg of 5 (352 μmol), 203 mg of 14 (0.70 mmol) and 146 mg of sodium 2-ethylhexanoate (0.77 mmol) in 2 ml of THF are successively introduced into a Wheaton tube, with agitation and under an argon atmosphere. The agitation is maintained at AT for 24 h. The mixture is evaporated to dryness and then purified by chromatography on a silica cartridge (20 g), elution being carried out with CH$_2$Cl$_2$/MeOH (as an MeOH gradient: 1 to 10%). 150 mg of expected product 15 are recovered.

$^1$H NMR (300 MHz, DMSO-d$_6$), δ(ppm): (a 60%-40% mixture of isomers): 0.99 (s, 9H); 1.23 (s, 1.2H); 1.25 (s, 1.8H); 1.28 (s, 1.2H); 1.30 (s, 1.8H); 2.11 (m, 1H); 2.32 (m, 1H); 2.78 (m, 2H); from 3.22 to 3.35 (m masked, 1H); 3.25 (s, 1.8H); 3.27 (s, 1.2H); 3.74 (d, J=8.5 Hz, 0.6H); 3.77 (d, J=8.5 Hz, 0.4H); 3.91 (broad d, J=8.5 Hz, 0.4H); 3.96 (broad d, J=8.5 Hz, 0.6H); from 4.20 to 4.44 (m, 3H); 5.44 (dd, J=7.0 and 16.0 Hz, 1H); 5.68 (d, J=16.0 Hz, 1H); 7.10 (d, J=8.5 Hz, 1H); 7.35 (t, J=7.5 Hz, 1H); 7.46 (t, J=7.5 Hz, 2H); 7.57 (broad d, J=8.5 Hz, 1H); 7.62 (broad s, 1H); 7.67 (d, J=7.5 Hz, 2H); 8.09 (d, J=7.5 Hz, 0.6H); 8.15 (d, J=7.5 Hz, 0.4H); 9.87 (s, 0.4H); 9.92 (s, 0.6H).

Step 4: Preparation of N-(7-phenyl-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide (Ex4) and Ex4a & Ex4b

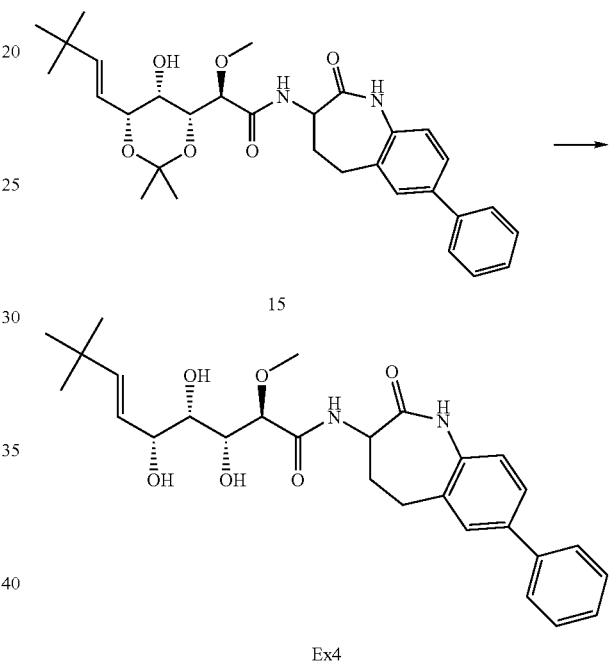

150 mg of 15 (280 μmol) in 1,4 ml of THF and 2.78 ml of 1N hydrochloric acid are introduced into a 20 ml round-bottomed flask, with stirring and under argon. The stirring is maintained for 4 h at AT. The medium is neutralized with NaOH (1N), to pH 7, and extracted with 2 times 5 ml of EtOAc. The combined organic phases are dried over MgSO$_4$, filtered and evaporated to dryness. The crude is chromatographed on a silica cartridge (10 g) with an eluent of CH$_2$Cl$_2$/MeOH (as an MeOH gradient of 1 to 10%). 85 mg of expected product Ex4 are recovered. 58 mg of Ex4 are separated by preparative chiral HPLC (Chirapad AD-H 5 μm 250×4.6 mm, flow rate 1 ml/min, mobile phase: 70% heptane-30% EtOH, 0.1% TEA), to give 16 mg of Ex4a (tr=13.42 min) and 40 mg of Ex4b (tr=18.96 min).

ES: 497 MH$^+$.

Ex4: $^1$H NMR (400 MHz, DMSO-d$_6$), δ(ppm): (a 70%-30% mixture of isomers) 0.95 (s, 2.7H); 0.99 (s, 6.3H); 2.11 (m, 1H); 2.35 (m, 1H); 2.79 (m, 2H); 3.23 (s, 3H); from 3.25 to 3.35 (m masked, 1H); 3.53 (m, 1H); 3.68 (d, J=8.5 Hz, 0.3H); 3.70 (d, J=8.5 Hz, 0.7H); 3.95 (m, 1H); from 4.22 to 4.33 (m, 2.3H); 4.41 (d, J=6.0 Hz, 0.7H); 4.55 (m, 1H); 5.30 (m, 1H); 5.61 (d, J=16.0 Hz, 0.3H); 5.63 (d, J=16.0 Hz, 0.7H); 7.10 (d, J=8.5 Hz, 1H); 7.35 (t, J=7.5 Hz, 1H); 7.46 (t, J=8.0

Hz, 2H); 7.57 (dd, J=2.5 and 8.5 Hz, 1H); 7.62 (broad s, 1H); 7.67 (d, J=8.0 Hz, 2H); 8.04 (d, J=7.5 Hz, 1H); 9.93 (s, 0.3H); 9.99 (s, 0.7H).

Ex4a: ¹H NMR (400 MHz, DMSO-d₆), δ(ppm): 0.95 (s, 9H); 2.10 (m, 1H); 2.37 (m, 1H); 2.79 (m, 2H); 3.24 (s, 3H); from 3.27 to 3.33 (m masked, 1H); 3.51 (m, 1H); 3.68 (d, J=7.5 Hz, 1H); 3.93 (m, 1H); from 4.22 to 4.32 (m, 3H); 4.54 (d, J=4.5 Hz, 1H); 5.29 (dd, J=7.0 and 16.0 Hz, 1H); 5.61 (d, J=16.0 Hz, 1H); 7.10 (d, J=8.0 Hz, 1H); 7.35 (t, J=7.5 Hz, 1H); 7.46 (t, J=7.5 Hz, 2H); 7.56 (dd, J=2.0 and 8.0 Hz, 1H); 7.62 (d, J=2.0 Hz, 1H); 7.67 (m, 2H); 8.02 (d, J=7.5 Hz, 1H); 9.93 (s, 1H).

EX4a (2R,3R,4S,5R,6E)-3,4,5-trihydroxy-2-methoxy-8,8-dimethyl-N-[(3S)-2-oxo-7-phenyl-2,3,4,5-tetrahydro-1H-1-benzazepin-3-yl]non-6-enamide

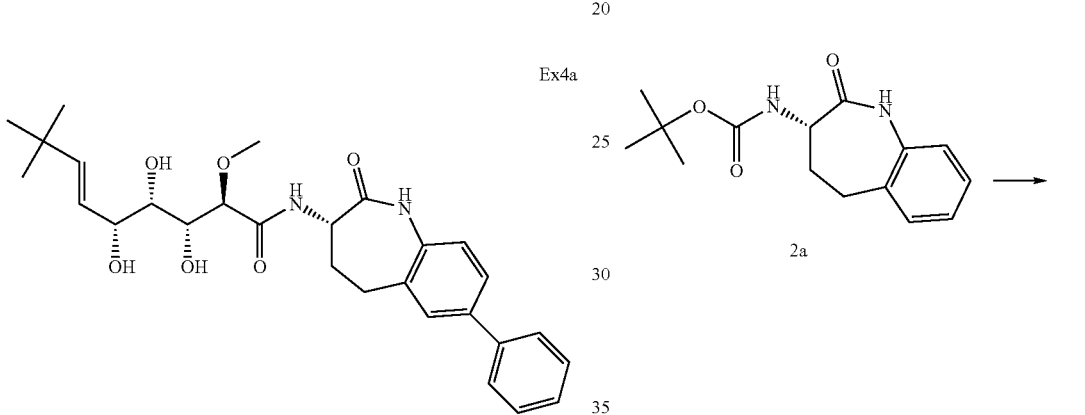

Ex4a

Step 1: Preparation of tert-butyl [(3S)-2-oxo-2,3,4,5-tetrahydro-1H-1-benzazepin-3-yl]carbamate (2a)

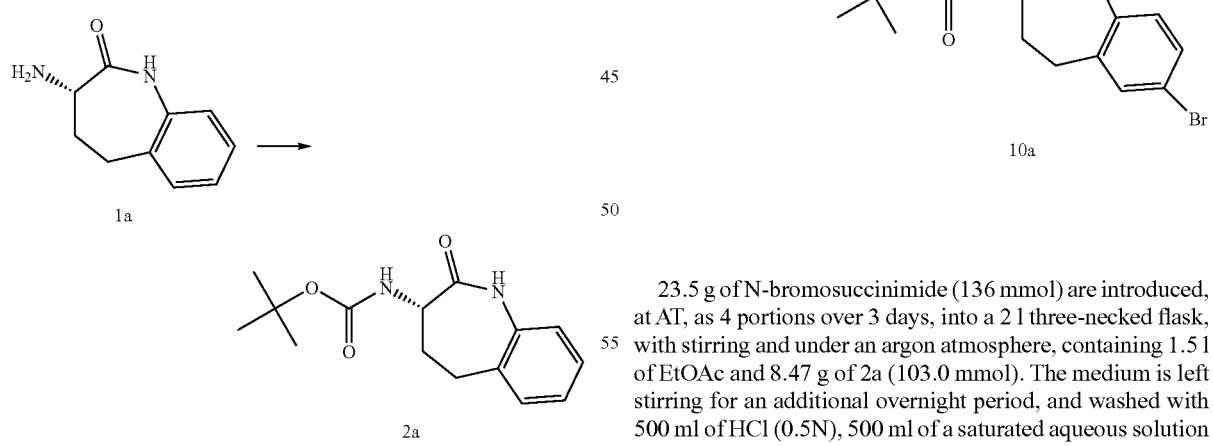

16 ml of TEA (113.5 mmol), and a solution of 24.77 g of tBoc₂O (113.5 mmol) in 500 ml of CHCl₃ are added at 0° C. to a 2 l round-bottomed flask containing 20.0 g of 1a (113.5 mmol) ((s)-3-amino-1,3,4,5,-tetrahydro-2H-1-benzazepin-2-one, prepared according to the procedures described in J. Org. Chem. 1997, 62, 8271), and 500 ml of CHCl₃. The medium is stirred overnight. The reaction medium is washed with 500 ml of HCl (0.5N) and 500 ml of water. The organic phase is dried over MgSO₄, filtered and evaporated to dryness, and the solids are disintegrated with 200 ml of isopropyl ether. After filter-drying, 30.02 g of 2a (off-white solid) are obtained.

[α]_D: −229.0+/−2.5 (c=1.852 mg/0.5 ml MeOH)

¹H NMR (400 MHz, DMSO-d₆), δ(ppm): 1.33 (s, 9H); from 1.98 to 2.25 (m, 2H); from 2.59 to 2.71 (m, 2H); 3.89 (m, 1H); 6.90 (d, J=8.0 Hz, 1H); 7.00 (d, J=7.5 Hz, 1H); 7.11 (d, J=7.5 Hz, 1H); from 7.20 to 7.30 (m, 2H); 9.68 (s, 1H).

Step 2: Preparation of tert-butyl [(3S)-7-bromo-2-oxo-2,3,4,5-tetrahydro-1H-1-benzazepin-3-yl]carbamate (10a)

23.5 g of N-bromosuccinimide (136 mmol) are introduced, at AT, as 4 portions over 3 days, into a 2 l three-necked flask, with stirring and under an argon atmosphere, containing 1.5 l of EtOAc and 8.47 g of 2a (103.0 mmol). The medium is left stirring for an additional overnight period, and washed with 500 ml of HCl (0.5N), 500 ml of a saturated aqueous solution of NaHCO₃ and 500 ml of water. The organic phase is dried over MgSO₄, filtered and then evaporated to dryness. 38 g of brown foam are obtained. The product is purified by chromatography on a silica cartridge (600 g), elution being carried out with heptane/EtOAc (70/30). 20.46 g of expected product 10a (white solid) are recovered.

¹H NMR (400 MHz, DMSO-d₆), δ(ppm): 1.34 (s, 9H); 2.05 (m, 1H); 2.20 (m, 1H); from 2.56 to 2.73 (m, 2H); 3.87

(m, 1H); 6.97 (m, 2H); 7.45 (dd, J=2.0 and 8.0 Hz, 1H); 7.51 (d, J=2.0 Hz, 1H); 9.75 (s, 1H).

Step 3: Preparation of tert-butyl [(3S)-2-oxo-7-phenyl-2,3,4,5-tetrahydro-1H-1-benzazepin-3-yl]carbamate (13a)

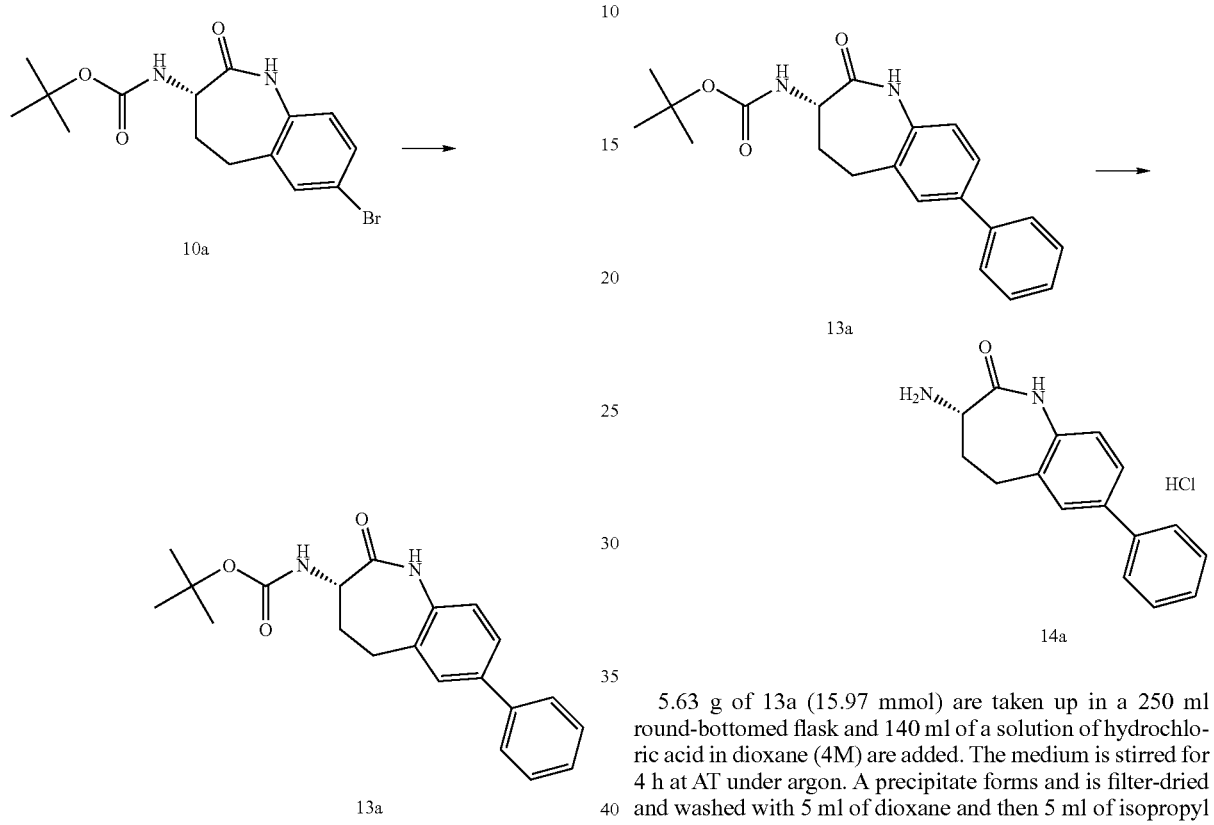

2.643 g of phenylboronic acid (21.68 mmol), 402 mg of 1,1'-bis(diphenyl-phosphino)ferrocene palladium chloride ($C_{35}H_{30}Cl_4FeP_2Pd$, Mw 816.65, 0.493 mmol) and 25.69 g of caesium carbonate (78.84 mmol) are introduced into a 500 ml round-bottomed flask, with stirring and under an argon atmosphere, containing 142 ml of water, 42 ml of dioxane and 7.0 g of 10a (19.71 mmol). The medium is heated at 100° C. with stirring for 4 h. The dioxane is concentrated under vacuum, 100 ml of distilled water are added, and the mixture is extracted with 2×200 ml of EtOAc. The organic phase is dried over $MgSO_4$, filtered and evaporated to dryness. 7 g of a brown solid are obtained, which solid is crystallized from 55 ml of toluene under hot conditions. After having left the product to stand at AT overnight, the needles are filter-dried, and washed with 5 ml of toluene and with 5 ml of isopropyl ether. After vacuum drying, 5.63 g of expected product 13a are obtained.

Mp=198.6+/−1° C.

$[\alpha]_D$: −157.0+/−2.1 (c=2.332 mg/0.5 ml MeOH)

MS: m/z=353 [M+H]$^+$ $^1$H NMR (400 MHz, DMSO-d$_6$), δ(ppm): 1.34 (s, 9H); 2.09 (m, 1H); 2.25 (m, 1H); from 2.65 to 2.80 (m, 2H); 3.94 (m, 1H); 6.95 (d, J=8.0 Hz, 1H); 7.09 (d, J=8.5 Hz, 1H); 7.35 (t, J=7.5 Hz, 1H); 7.46 (t, J=7.5 Hz, 2H); 7.54 (dd, J=2.0 and 8.5 Hz, 1H); 7.59 (d, J=2.0 Hz, 1H); 7.67 (d, J=7.5 Hz, 2H); 9.76 (s, 1H).

Step 4: Preparation of (3S)-3-amino-7-phenyl-1,3,4,5-tetrahydro-2H-1-benzazepin-2-one hydrochloride (14a)

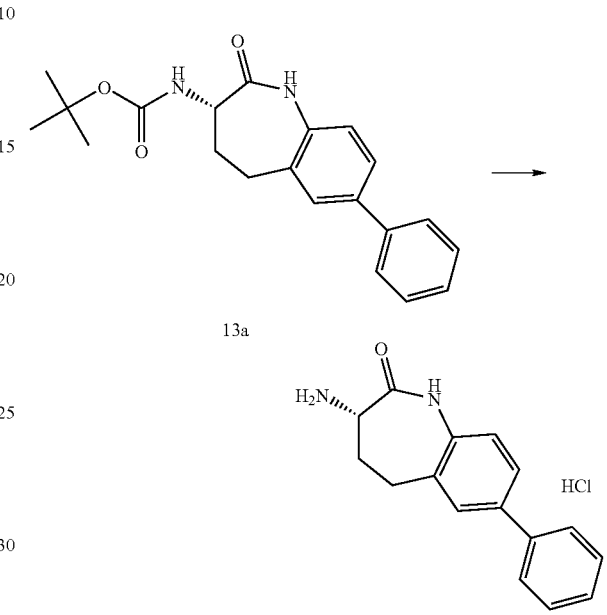

5.63 g of 13a (15.97 mmol) are taken up in a 250 ml round-bottomed flask and 140 ml of a solution of hydrochloric acid in dioxane (4M) are added. The medium is stirred for 4 h at AT under argon. A precipitate forms and is filter-dried and washed with 5 ml of dioxane and then 5 ml of isopropyl ether. After drying, 5.7 g of amine 14a in hydrochloride form are obtained.

Mp=198.6+/−1° C.

$[\alpha]_D$: −292.0+/−3.2 (c=1.894 mg/0.5 ml MeOH)

$^1$H NMR (400 MHz, DMSO-d$_6$), δ(ppm): 2.19 (m, 1H); 2.57 (m, 1H); from 2.72 to 2.91 (m, 2H); 3.78 (m, 1H); 7.13 (d, J=8.5 Hz, 1H); 7.38 (t, J=7.5 Hz, 1H); 7.48 (t, J=7.5 Hz, 2H); 7.60 (dd, J=2.0 and 8.5 Hz, 1H); 7.69 (m, 3H); 8.29 (broad s, 3H); 10.35 (s, 1H).

Step 5: Preparation of (2R,3R,4S,5R,6E)-3,4,5-trihydroxy-2-methoxy-8,8-dimethyl-N-[(3S)-2-oxo-7-phenyl-2,3,4,5-tetrahydro-1H-1-benzazepin-3-yl]non-6-enamide (Ex4a)

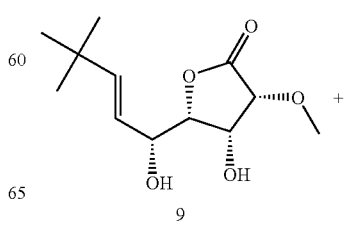

-continued

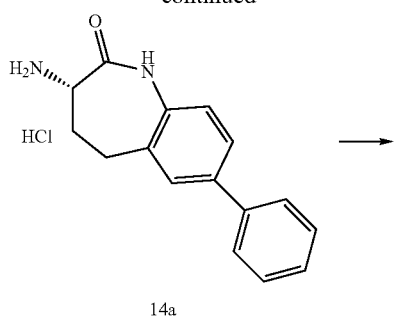

14a

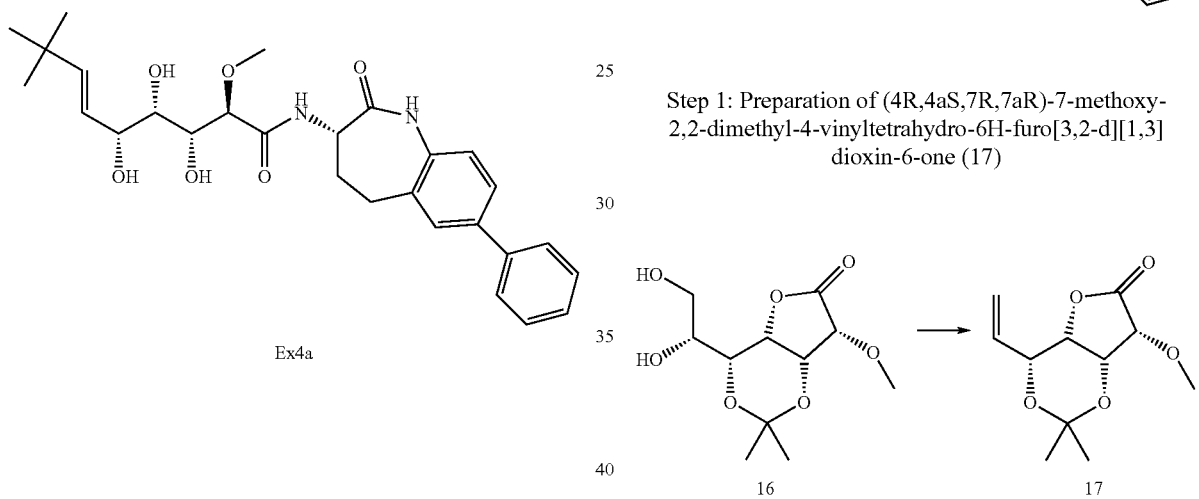

Ex4a 2.3 g of 9 (9.42 mmol), 2.72 g of 14a (9.42 mmol) and 3.63 g of sodium 2-ethylhexanoate (21.84 mmol) in 50.0 ml of THF are successively introduced into a 150 ml round-bottomed flask, with stirring and under an argon atmosphere. The stirring is maintained at AT for 48 h. The reaction medium is directly evaporated to dryness. The crude is chromatographed on a silica cartridge (300 g, eluent EtOAc), and 3.7 g of a white solid are obtained, which solid is repurified on a silica cartridge (240 g, eluent CH$_2$Cl$_2$/MeOH—as an MeOH gradient: 1 to 5%). 3.23 g of expected product Ex4a (white solid) are recovered.

$[\alpha]_D$: −54.6+/−0.9 (c=2.989 mg/0.5 ml MeOH)

MS: m/z=497 [M+H]$^+$ $^1$H NMR (400 MHz, DMSO-d$_6$), δ(ppm): 0.95 (s, 9H); 2.11 (m, 1H); 2.38 (m, 1H); 2.79 (m, 2H); 3.24 (s, 3H); 3.30 (m masked, 1H); 3.52 (m, 1H); 3.69 (d, J=8.0 Hz, 1H); 3.93 (m, 1H); from 4.20 to 4.32 (m, 3H); 4.53 (d, J=5.5 Hz, 1H); 5.30 (dd, J=7.5 and 16.0 Hz, 1H); 5.62 (d, J=16.0 Hz, 1H); 7.10 (d, J=8.5 Hz, 1H); 7.35 (t, J=7.5 Hz, 1H); 7.45 (t, J=7.5 Hz, 2H); 7.57 (dd, J=2.0 and 8.5 Hz, 1H); 7.62 (d, J=2.0 Hz, 1H); 7.68 (d, J=7.5 Hz, 2H); 8.02 (d, J=8.0 Hz, 1H); 9.92 (s, 1H).

EX5

(2R,3R,4S,5R,6E)-7-cyclopentyl-3,4,5-trihydroxy-2-methoxy-N-[(3S)-2-oxo-7-phenyl-2,3,4,5-tetrahydro-1H-1-benzazepin-3-yl]hept-6-enamide

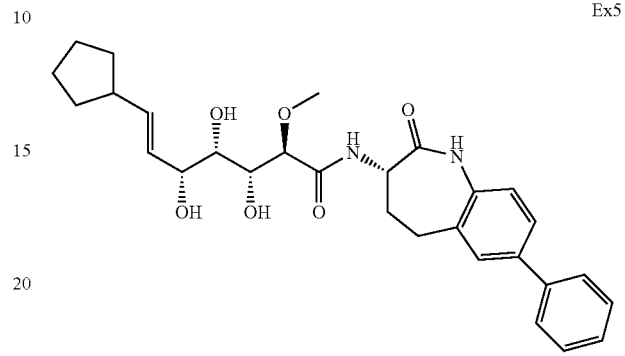

Ex5

Step 1: Preparation of (4R,4aS,7R,7aR)-7-methoxy-2,2-dimethyl-4-vinyltetrahydro-6H-furo[3,2-d][1,3]dioxin-6-one (17)

A 4000 ml round-bottomed flask, equipped with a mechanical stirrer, is filled, under nitrogen, with 178.2 g of PPh$_3$ (0.679 mol), 84.1 g of imidazole (1.235 mol) and 2430 ml of anhydrous THF. 156.8 g of doubly sublimed iodine (0.618 mol) are carefully added while maintaining the temperature of the reaction mixture at 30° C. This medium is brought to reflux (66° C.) for 1 h, and then 81 g of 16 (0.309 mol) (which can be prepared according to the procedures described in Org. Process Res. Dev. 2003, 7(6), 856-865) are gradually added at 66° C.+/−2° C. The homogeneous mixture thus obtained is refluxed for 3 h. It is allowed to return to 20° C.+/−5° C., and then 1000 ml of a 10% NaHCO$_3$ solution (effervescence, athermic) (pH 8.0-8.5) are run in. 185.5 g of Na$_2$S$_2$O$_3$ are subsequently added until almost complete discoloration is obtained (appearance of a mineral precipitate). After stirring at 20° C.+/−5° C. for 30 minutes, the solid is filtered off and rinsed with THF. The THF/H$_2$O filtrate is partially concentrated in a rotary evaporator at a temperature below 35° C. The aqueous concentrate is saturated with NaCl and extracted with 1500 ml of CH$_2$Cl$_2$. The organic phase is dried over MgSO$_4$, filtered and evaporated to dryness. The residue is taken up in 2000 ml of a mixture of H$_2$O/acetone (75/25), the insoluble materials are filtered off and rinsed with a the mixture of H₂O/acetone (75/25). The filtrates are concentrated in a rotary evaporator at 50° C. and 20 mbar, and filtered again over a sintered glass funnel (porosity No. 4). The aqueous phase is saturated with NaCl and is extracted 3 times with CH₂Cl₂ (1000 ml, 500 ml and 250 ml). The organic phases are combined, dried over MgSO₄, filtered and evaporated to dryness, to give 60 g of crude product, which is dissolved in 250 ml de CH₂Cl₂. 30 g of silica are then added to the solution. After stirring for 15 minutes, the silica is filtered off, and rinsing is performed twice with CH₂Cl₂ (250 ml and 100 ml). The filtrate is concentrated to dryness and dried under 1 mbar at 20° C., to give 54.8 g of expected product 17 (white solid).

¹H NMR (300 MHz, DMSO-d₆), δ(ppm): 5.85 (m, 1H); 5.35 (d, 1H); 5.25 (d, 1H); 4.80 (m, 1H); 4.69 (m, 1H); 4.43 (d, 1H); 4.22 (m, 1H); 3.40 (s, 3H); 1.49 (s, 3H); 1.30 (s, 3H).

Step 2: Preparation of (3R,4R,5S)-4-hydroxy-5-[(1R)-1-hydroxyprop-2-en-1-yl]-3-methoxydihydrofuran-2(3H)-one (18)

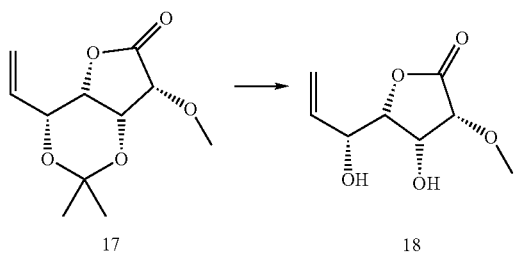

17            18

10 ml of TFA are added dropwise, at 0° C., to a 100 ml round-bottomed flask containing 1.0 g of 17 (4.38 mmol), 10 ml of water and 14 ml of THF. The medium is left to return to AT and stirred overnight. The medium is then concentrated at reduced pressure, at AT, and 50 ml of water are added, and the mixture is frozen and lyophilized. The lyophilizate is made into a paste in heptane, in the presence of a minimum amount of methanol, after the solvents have been evaporated off. 778 mg of expected product 18 (white solid) are obtained.

MS: m/z=211 [M+Na]⁺, 189 [M+H]⁺

¹H NMR (400 MHz, DMSO-d₆), δ(ppm): 3.42 (s, 3H); 3.98 (dd, J=2.5 and 9.0 Hz, 1H); from 4.25 to 4.34 (m, 3H); 5.22 (dm, J=10.5 Hz, 1H); 5.29 (d, J=5,0 Hz, 1H); 5.44 (d partially masked, J=16.5 Hz, 1H); 5.46 (m, 1H); 5.97 (m, 1H).

Step 3: Preparation of (3R,4R,5S)-5-[(1R,2E)-3-cyclopentyl-1-hydroxyprop-2-en-1-yl]-4-hydroxy-3-methoxydihydrofuran-2(3H)-one (19)

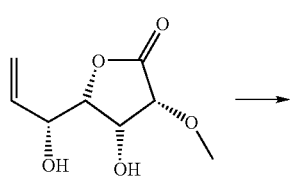

18

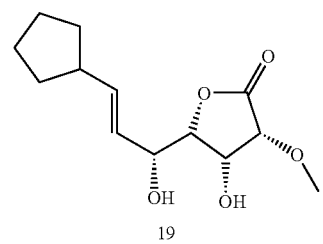

19

100 mg (0.53 mmol) of 18, 4 ml of CH₂Cl₂, 726 μl (5.3 mmol) of vinylcyclopentane and then 90.2 mg (106 μmol) of second-generation Grubbs catalyst are introduced into a 5 ml vial. The solution is microwave-heated at 60° C. for 10 min. The solvent is subsequently evaporated to dryness under reduced pressure and the residue is then purified on a Biotage 12-M silica column (eluent: 40/60 Hept/EtOAc). The product 19 (76.3 mg, Rf=0.35 under the elution conditions used) is obtained in the form of a brown solid.

MS: m/z=279 [M+Na]⁺, 257 [M+H]⁺

¹H NMR (300 MHz, DMSO-d₆), δ(ppm): 5.82 (dd, 1H, J=8 Hz and 16 Hz), 5.50 (dd, 1H, J=6 Hz and 16 Hz), 5.39 (d, 1H, J=4.5 Hz), 5.15 (d, 1H, J=6 Hz), 4.27 (m, 3H), 3.95 (dd, 1H, J=3 Hz and 8 Hz), 3.41 (s, 3H), 2.43 (m, 1H), 1.73 (m, 2H), 1.56 (m, 4H), 1.26 (m, 2H).

Step 4: Preparation of (2R,3R,4S,5R,6E)-7-cyclopentyl-3,4,5-trihydroxy-2-methoxy-N-[(3S)-2-oxo-7-phenyl-2,3,4,5-tetrahydro-1H-1-benzazepin-3-yl]hept-6-enamide (Ex5)

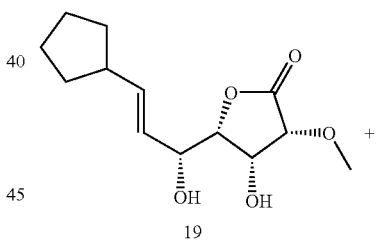

19

+

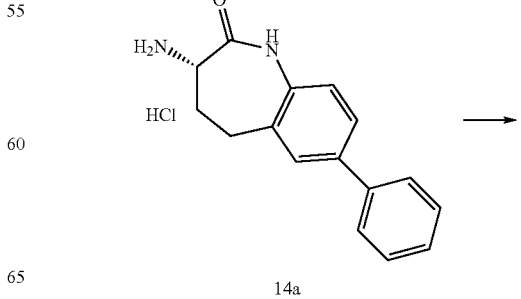

14a

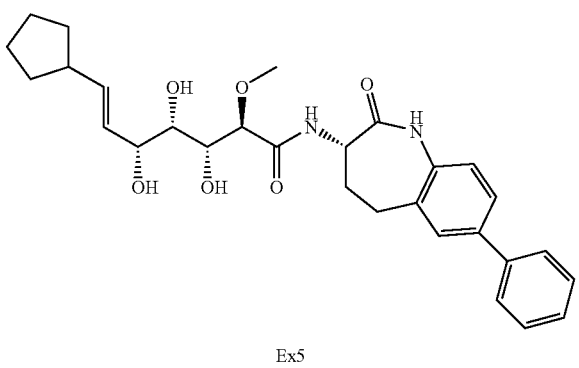

Ex5

100 mg of 19 (0.39 mmol), 112.6 mg of 14a (0.39 mmol) and 162 mg of sodium 2-ethylhexanoate (0.98 mmol) in 2.0 ml of THF are successively introduced into a Wheaton tube, with agitation and under an argon atmosphere. The agitation is maintained at AT for 24 h. The reaction medium is directly evaporated to dryness. The crude is chromatographed on a silica cartridge (12 g, eluent EtOAc). 92 mg of expected product Ex5 (white solid) are obtained.

ES: m/z=531 MNa$^+$; m/z=509 MH$^+$.

$^1$H NMR (400 MHz, DMSO-d$_6$), δ(ppm): from 1.13 to 1.73 (m, 8H); 2.11 (m, 1H); from 2.29 to 2.45 (m, 2H); from 2.70 to 2.85 (m, 2H); 3.23 (s, 3H); 3.30 (m masked, 1H); 3.50 (m, 1H); 3.69 (d, J=8.0 Hz, 1H); 3.92 (m, 1H); from 4.19 to 4.38 (m, 3H); 4.52 (broad s, 1H); 5.36 (dd, J=7.5 and 16.0 Hz, 1H); 5.58 (dd, J=8.0 and 16.0 Hz, 1H); 7.10 (d, J=8.5 Hz, 1H); 7.36 (t, J=7.5 Hz, 1H); 7.46 (t, J=7.5 Hz, 2H); 7.58 (broad d, J=8.5 Hz, 1H); 7.62 (broad s, 1H); 7.69 (d, J=7.5 Hz, 2H); 8.02 (d, J=8.0 Hz, 1H); 9.92 (s, 1H).

EX6

(2R,3R,4S,5R,6E)-7-cyclopentyl-3,4,5-trihydroxy-2-methoxy-N-[(3S-1-methyl-2-oxo-2,3,4,5-tetrahydro-1H-1-benzazepin-3-yl]hept-6-enamide

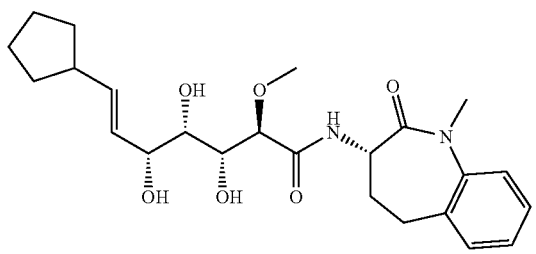

Ex5

Step 1: Preparation of tert-butyl [(3S)-1-methyl-2-oxo-2,3,4,5-tetrahydro-1H-1-benzazepin-3-yl]carbamate (7a)

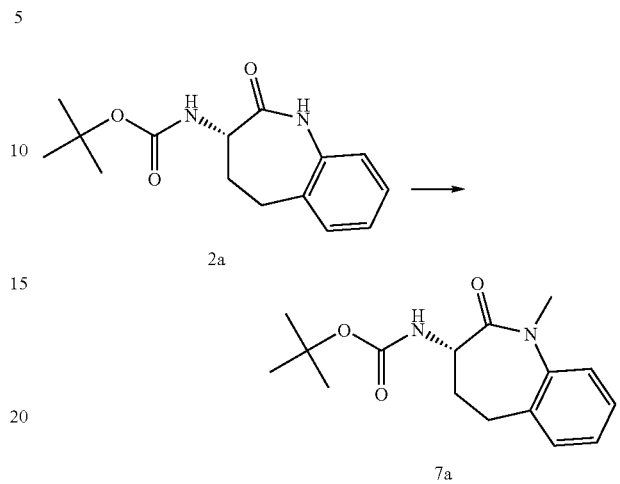

0.898 mg of sodium hydride in suspension at 60% in oil (22.44 mmol) is introduced, at AT, into a 500 ml round-bottomed flask, with stirring and under an argon atmosphere, containing 260 ml of THF and 6.2 g of 2a (22.44 mmol). The medium is stirred for 1 h and then 3.823 g (26.94 mmol) of methyl iodide are added. The medium is left stirring overnight, 500 ml of EtOAc are added and the organic phase is washed twice with 500 ml of water. The organic phase is dried over MgSO$_4$, filtered and then evaporated to dryness. 6.85 g of crude product are obtained. After chromatography on a silica cartridge (250 g, eluent heptane/EtOAc—as an EtOAc gradient: 10 to 50%). 4.47 g of product 7a (white solid) are obtained.

Mp=133.2+−1° C.
[α]$_D$: −204.8+/−2.2 (c=2.484 mg/0.5 ml MeOH)

Step 2: Preparation of (3S)-3-amino-1-methyl-1,3,4,5-tetrahydro-2H-1-benzazepin-2-one hydrochloride (8a)

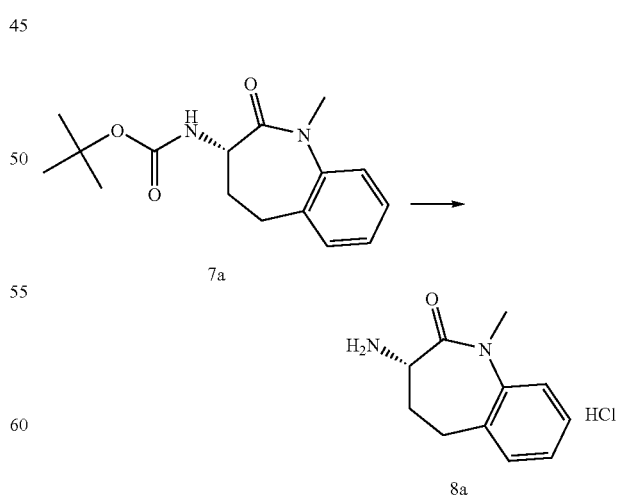

4.36 g of 7a (15.01 mmol) are taken up in a 250 ml round-bottomed flask and 110 ml of a solution of hydrochloric acid in dioxane (4M) are added. The mixture is stirred for 4 h at AT under argon. After the solvent has been evaporated off, the solid is disintegrated with 25 ml of isopropyl ether, and filter-dried over sintered glass. After drying, 3.1 g of amine 8a in hydrochloride form are obtained, which amine is used directly for the following step.

Mp=221.7+/−1° C.

[α]$_D$: −257.1+/−2.8 (c=2.696 mg/0.5 ml MeOH).

Step 3: Preparation of (2R,3R,4S,5R,6E)-7-cyclo-pentyl-3,4,5-trihydroxy-2-methoxy-N-[(3S)-1-methyl-2-oxo-2,3,4,5-tetrahydro-1H-1-benzazepin-3-yl] hept-6-enamide (Ex6)

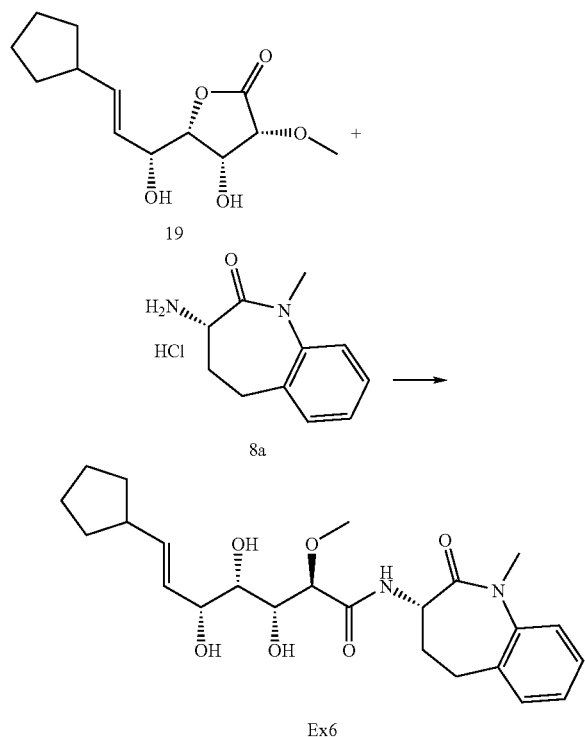

100 mg of 19 (0.39 mmol), 88.42 mg of 8a (0.39 mmol) and 162 mg of sodium 2-ethylhexanoate (0.98 mmol) in 2.0 ml of THF are successively introduced into a Wheaton tube, with agitation and under an argon atmosphere. The agitation is maintained at AT for 24 h. The reaction medium is directly evaporated to dryness. The crude is chromatographed on a silica cartridge (12 g, eluent EtOAc), and 60 mg of expected product Ex6 (white solid) are obtained.

ES: m/z=447 MH$^+$.

$^1$H NMR (500 MHz, DMSO-d$_6$), δ(ppm): 1.21 (m, 2H); from 1.41 to 1.73 (m, 6H); 2.03 (m, 1H); 2.20 (m, 1H); 2.37 (m, 1H); from 2.60 to 2.75 (m, 2H); 3.21 (s, 3H); from 3.25 to 3.35 (m masked, 1H); 3.30 (s, 3H); 3.48 (m, 1H); 3.66 (d, J=8.0 Hz, 1H); 3.91 (m, 1H); 4.20 (m, 1H); 4.29 (m, 2H); 4.53 (d, J=4.0 Hz, 1H); 5.35 (dd, J=7.5 and 16.0 Hz, 1H); 5.57 (dd, J=8.5 and 16.0 Hz, 1H); 7.23 (m, 1H); 7.31 (d, J=7.5 Hz, 1H); 7.39 (m, 2H); 8.04 (d, J=8.0 Hz, 1H).

Biological Activity of the Products Prepared:

On the day the application was filed, it was measured that the CaCO$_2$-TC7 of the product of Example 4a (Papp single point=48.10$^{-7}$ cm·sec$^{-1}$) is better than that of the product of Example 22a (Papp single point=6.10$^{-7}$ cm·sec$^{-1}$) described in patent application WO 2006/056696.

The antiproliferative activity of the products of the examples of Table 1 was determined by measuring the inhibition of the cell proliferation of HCT116 cells. The cells are seeded into a cell culture medium at a concentration of 10 000 cells per well, in 0.17 ml of medium, and 20 μl of test product, at various concentrations and 10 μl of thymidine [methyl-14C] (100 μCi/ml—specific activity 47.90 mCi/mmol; NEN Technologies reference NEC568 batch 3550-001) are added and the cells are then incubated at 37° C. and 5% CO$_2$.

Medium used for the HCT116 cell culture: DMEM medium, 2 mM L-glutamine, 200 IU/ml penicillin, 200 μg/ml streptomycin and 10% (V/V) foetal calf serum (Life Technologies).

After 96 hours, the $^{14}$C-thymidine incorporation is counted in a 1450 Microbeta Wallac Trilux liquid scintillation counter. The results R are expressed in cpm (counts per minute) and converted to percentage growth inhibition GI % by firstly subtracting the mean of the number of cpm of the wells without cells B and then dividing by the number of cpm of the wells of the nontreated cells C comprising 20 μl of product diluting medium containing 1% of ethanol (GI %=(R−B)×100/C %).

The IC50 values are calculated using equation 205 of the XLFit software (IDBS company, UK) by nonlinear regression analysis using the Marquardt algorithm (Donald W. MARQUARDT, J. Soc. industry. appl, vol 11, No. 2, June, 1963).

The products in Table 1 have an IC50 on HCT116 cells that is generally less than 30 μM, and preferably less than 100 nM. For example, the product of Example 1 has an IC50 of 14 nM and the product of Example 3 has an IC50 of 58 nM. The product of Example 2 has an IC50 of 15 nM, the product of Example 3a has an IC50 of 32 nM, the product of Example 4 has an IC50 of 75 nM and the product of Example 4a has an IC50 of 14 nM.

TABLE 1

| Example | Structure |
|---|---|
| Ex1 | 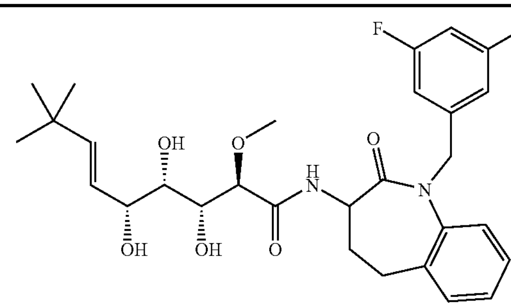 |

TABLE 1-continued
| Example | Structure |
|---|---|
| Ex2 | 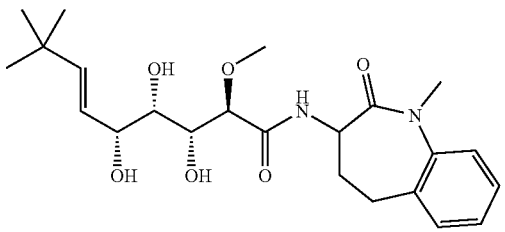 |
| Ex3 | 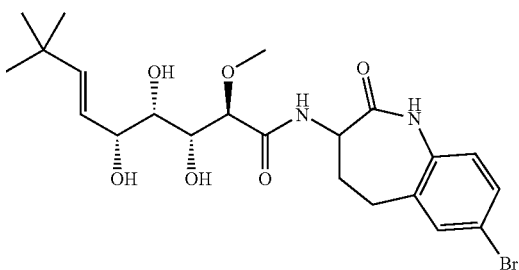 |
| Ex3a | 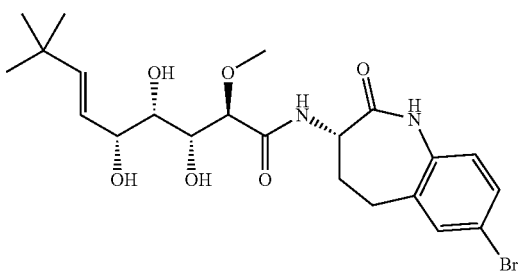 |
| Ex4 | 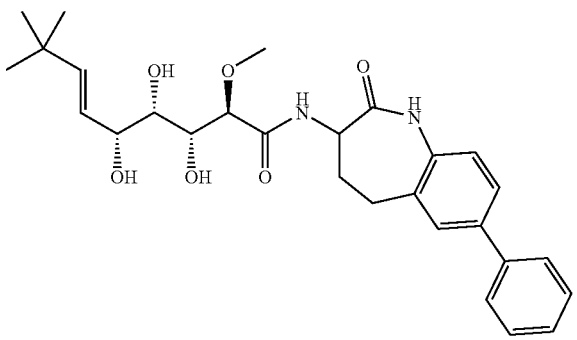 |
| Ex4a | 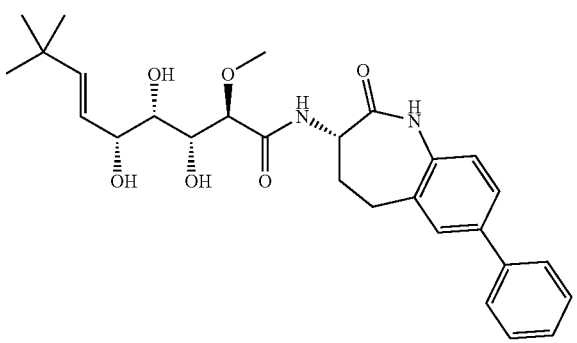 |

TABLE 1-continued

| Example | Structure |
|---|---|
| Ex5 | 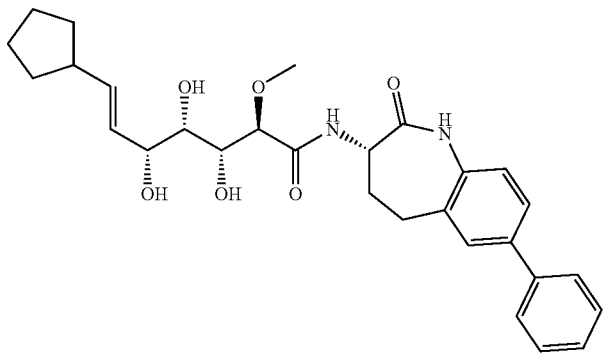 |
| Ex6 | 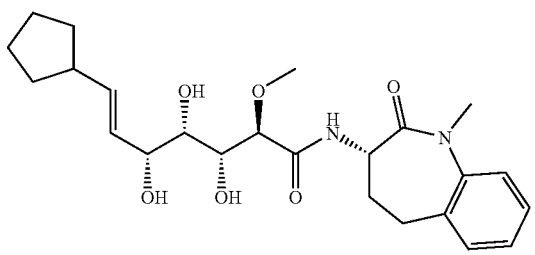 |

What is claimed is:

1. A compound of formula (I)

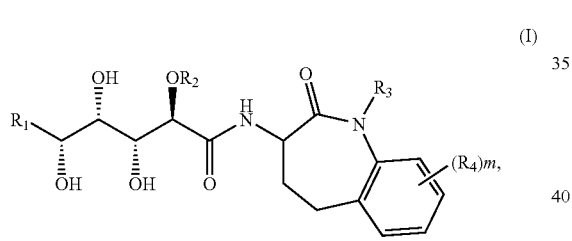

wherein:

a) $R_1$ is independently selected from the group consisting of $(C_1-C_{12})$alkyl, $(C_2-C_{12})$alkenyl, $(C_2-C_{12})$alkynyl, cycloalkyl, heterocyclyl, aryl, heteroaryl, cycloalkyl $(C_1-C_{12})$alkyl, cycloalkyl$(C_2-C_{12})$alkenyl, cycloalkyl $(C_2-C_{12})$alkynyl, heterocyclyl$(C_2-C_{12})$alkyl, heterocyclyl$(C_2-C_{12})$alkenyl, heterocyclyl$(C_2-C_{12})$alkynyl, aryl $(C_1-C_{12})$alkyl, aryl$(C_2-C_{12})$alkenyl, aryl$(C_2-C_{12})$alkynyl, heteroaryl$(C_1-C_{12})$alkyl, heteroaryl$(C_2-C_{12})$alkenyl, and heteroaryl$(C_2-C_{12})$alkynyl, the aryl group of each $R_1$ being optionally substituted with one or more halogens;

b) $R_2$ is selected from the group consisting of $(C_1-C_6)$alkyl, aryl$(C_1-C_6)$alkyl, heteroaryl$(C_1-C_6)$alkyl, aryl, heteroaryl, $(C_1-C_6)$alkylthio $(C_1-C_6)$alkyl, di$(C_1-C_6)$alkylamino$(C_1-C_6)$alkyl, aryloxy$(C_1-C_6)$alkyl, and $(C_1-C_6)$alkoxy$(C_1-C_6)$-alkyl;

c) $R_3$ is selected from the group consisting of H, COO$(R_5)$, CONH$(R_5)$, CO$(R_5)$, O$(R_5)$ and $R_5$;

d) $R_4$ is independently selected from the group consisting of, F, Cl, Br, N$(R_5)_2$, NO$_2$, CN, COO$(R_5)$, CON$(R_5)_2$, NHCO$(R_5)$, NHCOO$(R_5)$, OCONH$(R_5)$, O$(R_5)$ and $R_5$, or else two substituents $R_4$, attached to 2 adjacent carbons of the phenyl, together form a ring selected from a cycloalkyl, heterocyclyl, aryl and heteroaryl, optionally substituted with one or more $R_4$;

e) m has the value, 1, 2, 3 or 4;

f) $R_5$ is independently selected from a doublet of nonbonding electrons, H, $(C_1-C_{12})$alkyl, $(C_2-C_{12})$alkenyl, $(C_2-C_{12})$alkynyl, halo$(C_1-C_{12})$alkyl, aryl$(C_1-C_{12})$alkyl, heteroaryl$(C_1-C_{12})$alkyl, heteroarylaryl$(C_1-C_{12})$alkyl, aryl, heteroaryl and cycloalkyl, in which each $R_5$ is optionally substituted with at least one substituent selected from OH, halogen, $(C_1-C_4)$alkyl, $(C_1-C_4)$alkoxy, aryl$(C_1-C_4)$alkyl, aryl, heteroaryl$(C_1-C_4)$alkyl, heteroaryl, —N(CH$_3$)$_2$, —NH$_2$, CONH$_2$,

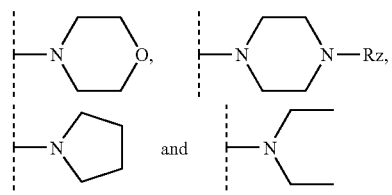

each of the Rz is independently selected from the group consisting of H, COO$(R_5)$, CONH$(R_5)$, CON$(R_5)_2$, CO$(R_5)$ and $R_5$, in which each $R_5$ is independently selected from $(C_1-C_4)$alkyl, halo$(C_1-C_4)$alkyl, aryl$(C_1-C_4)$alkyl and heteroaryl$(C_1-C_4)$alkyl, in which each $R_5$ is optionally substituted with a substituent selected from OH, halogen, $(C_1-C_4)$alkyl, $(C_1-C_4)$alkoxy, aryl$(C_1-C_4)$alkyl, aryl, heteroaryl$(C_1-C_4)$alkyl and heteroaryl; or a pharmaceutically acceptable acid addition salt of such compound, wherein a heteroaryl is a monocyclic or polycyclic heteroaromatic substituent containing from 1 to 13 carbon atoms and from 1 to 4 heteroatoms selected from oxygen, sulphur, nitrogen and selenium, and heterocyclyl is a saturated or partially unsaturated cyclic hydrocarbon based substituent containing from 1 to 13 carbon atoms and from 1 to 4 heteroatoms selected from oxygen, sulphur, nitrogen and selenium.

2. A compound according to claim 1, wherein $R_1$ is selected from —C($R_6$)=C($R_7$)($R_8$) in which $R_6$, $R_7$ and $R_8$ are independently selected from H, ($C_1$-$C_6$)alkyl, cycloalkyl, heterocyclyl, aryl and heteroaryl.

3. A compound according to claim 2, wherein $R_1$ is selected from (E)CH=CH—CH($CH_3$)($C_2H_5$), (E)CH=CH—CH($CH_3$)$_2$ and (E)CH=CH—C($CH_3$)$_3$.

4. A compound according to claim 2, wherein $R_1$ is selected from (E)C($CH_3$)=CH—CH($CH_3$)($C_2H_5$), (E)C($CH_3$)=CH—CH($CH_3$)$_2$ and (E)C($CH_3$)=CH—C($CH_3$)$_3$.

5. A compound according to claim 1 wherein $R_2$ is methyl.

6. A compound according to claim 2 wherein $R_2$ is methyl.

7. A compound according to claim 1 wherein $R_3$ is independently selected from: a methyl group or a (3,5-difluorophenyl)methyl group.

8. A compound according to claim 2 wherein $R_3$ is independently selected from: a methyl group or a (3,5-difluorophenyl)methyl group.

9. A compound according to claim 1 wherein $R_3$ is H.

10. A compound according to claim 2 wherein $R_3$ is H.

11. A compound according to claim 1 wherein $R_4$ is independently selected from: F, Cl, Br, phenyl and pyridinyl.

12. A compound according to claim 2 wherein $R_4$ is independently selected from: F, Cl, Br, phenyl and pyridinyl.

13. A compound according to claim 1 which is trihydroxy-2-methoxy-8,8-dimethylnon-6-enamide;
    N-((3S)-7-bromo-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide; or
    N-((3S)-7-phenyl-2-oxo-2,3,4,5-tetrahydro-1H-1-benzazepin-3-yl)-(E)-(2R,3R,4S,5R)-3,4,5-trihydroxy-2-methoxy-8,8-dimethylnon-6-enamide; or
    a pharmaceutically acceptable acid addition salt of such compound.

14. A compound according to claim 1 which is
    (2R,3R,4S,5R,6E)-7-cyclopentyl-3,4,5-trihydroxy-2-methoxy-N-[(3S)-1-methyl-2-oxo-2,3,4,5-tetrahydro-1H-1-benzazepin-3-yl]hept-6-enamide; or
    (2R,3R,4S,5R,6E)-7-cyclopentyl-3,4,5-trihydroxy-2-methoxy-N-[(3S)-2-oxo-7-phenyl-2,3,4,5-tetrahydro-1H-1-benzazepin-3-yl]hept-6-enamide;
    or a pharmaceutically acceptable acid addition salt of such compound.

15. A compound according to claim 1 which is
    a) in nonchiral form, or
    b) in racemic form, or
    c) in a form enriched in a stereoisomer, or
    d) in a form enriched in an enantiomer;
    and which is optionally salified.

16. A pharmaceutical composition comprising a compound according to claim 1 and at least one pharmaceutically acceptable excipient.

17. A pharmaceutical composition comprising a compound according to claim 13 and at least one pharmaceutically acceptable excipient.

18. A pharmaceutical composition comprising a compound according to claim 14 and at least one pharmaceutically acceptable excipient.

19. A process for preparing a compound according to claim 1 of formula (I) comprising the step of subjecting a compound of formula (II)

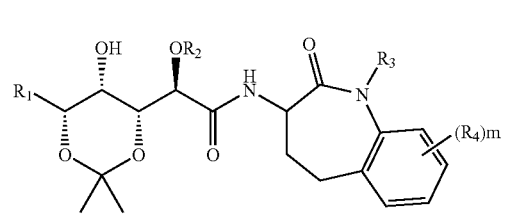

to hydrolysis so as to obtain a compound of formula (I).

20. A process according to claim 19 further comprising the step of reacting a compound of formula (III)

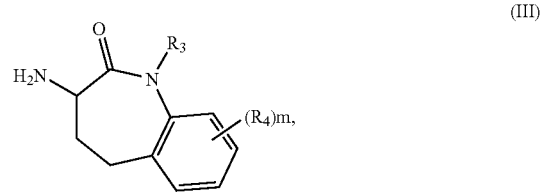

with a compound of formula (IV)

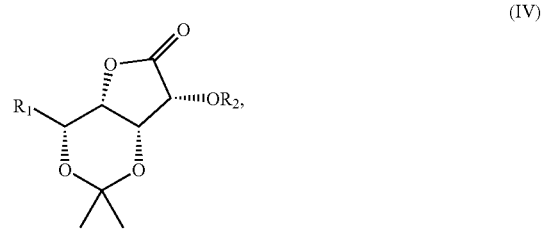

so as to obtain a compound of formula (II).

21. A process for preparing a compound according to claim 1 of formula (I), comprising the step of reacting a compound of formula (III)

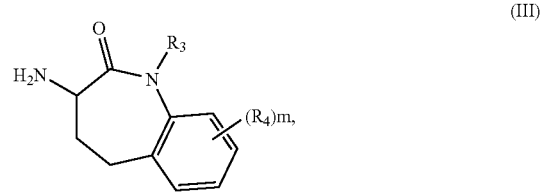

with a compound of formula (V)

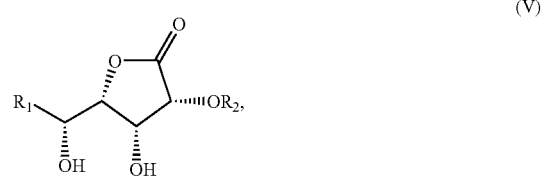

to obtain a compound of formula (I).

22. A process according to claim 21, further comprising the step of subjecting a compound of formula (IV)

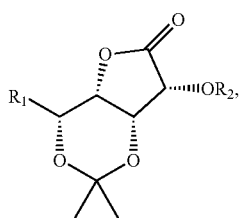

(IV)

to hydrolysis so as to obtain a compound of formula (V).

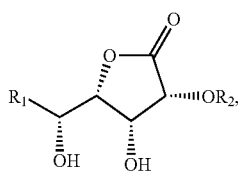

(V)

23. A process according to claim 21 further comprising the steps of subjecting a compound of formula (VII)

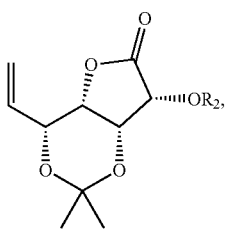

(VII)

to hydrolysis in order to obtain a compound of formula (VI)

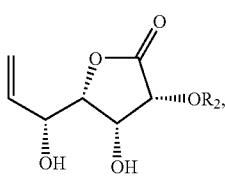

(VI)

and subjecting the compound of formula (VI) to metathesis in order to obtain a compound of formula (V)

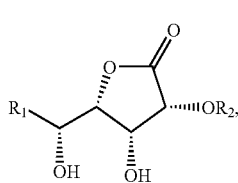

(V)

wherein $R_1$ is —CH=CH—$R'_1$ and $R'_1$ is a ($C_1$-$C_6$)alkyl, cycloalkyl, heterocyclyl, aryl or heteroaryl group.

24. A process according to claim 23 further comprising the step of subjecting a compound of formula (VIII)

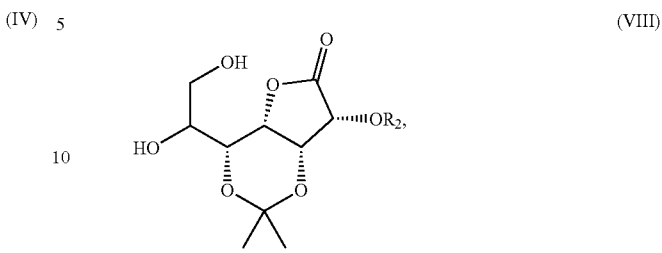

(VIII)

to double dehydration, in order to obtain a compound of formula (VII).

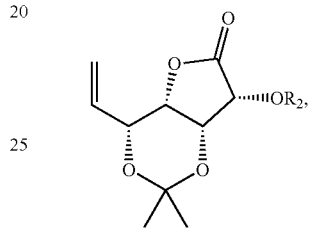

(VII)

25. A compound of formula (II)

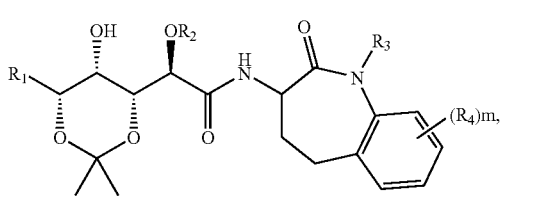

(II)

wherein:
a) $R_1$ is independently selected from the group consisting of ($C_1$-$C_{12}$)alkyl, ($C_2$-$C_{12}$)alkenyl, ($C_2$-$C_{12}$)alkynyl, cycloalkyl, heterocyclyl, aryl, heteroaryl, cycloalkyl($C_2$-$C_{12}$)alkyl, cycloalkyl($C_2$-$C_{12}$)alkenyl, cycloalkyl($C_2$-$C_{12}$)alkynyl, heterocyclyl($C_2$-$C_{12}$)alkyl, heterocyclyl($C_2$-$C_{12}$)alkenyl, heterocyclyl($C_2$-$C_{12}$)alkynyl, aryl($C_1$-$C_{12}$)alkyl, aryl($C_2$-$C_{12}$)alkenyl, aryl($C_2$-$C_{12}$)alkynyl, heteroaryl($C_1$-$C_{12}$)alkyl, heteroaryl($C_2$-$C_{12}$)alkenyl, and heteroaryl($C_2$-$C_{12}$)alkynyl, the aryl group of each $R_1$ being optionally substituted with one or more halogens;
b) $R_2$ is selected from the group consisting of ($C_1$-$C_6$)alkyl, aryl($C_1$-$C_6$)alkyl, heteroaryl($C_1$-$C_6$)alkyl, aryl, heteroaryl, ($C_1$-$C_6$)alkylthio ($C_1$-$C_6$)alkyl, di($C_1$-$C_6$)alkylamino($C_1$-$C_6$)alkyl, aryloxy($C_1$-$C_6$)alkyl, and ($C_1$-$C_6$)alkoxy($C_1$-$C_6$)-alkyl;
c) $R_3$ is selected from the group consisting of H, COO($R_5$), CONH($R_5$), CO($R_5$), O($R_5$) and $R_5$;
d) $R_4$ is independently selected from the group consisting of H, F, Cl, Br, N($R_5$)$_2$, NO$_2$, CN, COO($R_5$), CON($R_5$)$_2$, NHCO($R_5$), NHCOO($R_5$), OCONH($R_5$), O($R_5$) and $R_5$, or else two substituents $R_4$, attached to 2 adjacent carbons of the phenyl, together form a ring selected from a cycloalkyl, heterocyclyl, aryl and heteroaryl, optionally substituted with one or more $R_4$;

e) m has the value 0, 1, 2, 3 or 4;

f) $R_5$ is independently selected from a doublet of nonbonding electrons, H, $(C_1-C_{12})$alkyl, $(C_2-C_{12})$alkenyl, $(C_2-C_{12})$alkynyl, halo$(C_1-C_{12})$alkyl, aryl$(C_1-C_{12})$alkyl, heteroaryl$(C_1-C_{12})$alkyl, heteroarylaryl$(C_1-C_{12})$alkyl, aryl, heteroaryl and cycloalkyl, in which each $R_5$ is optionally substituted with at least one substituent selected from OH, halogen, $(C_1-C_4)$alkyl, $(C_1-C_4)$alkoxy, aryl$(C_1-C_4)$alkyl, aryl, heteroaryl$(C_2-C_4)$alkyl, heteroaryl, —N(CH$_3$)$_2$, —NH$_2$, CONH$_2$,

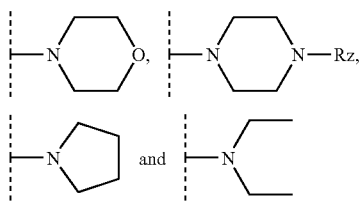

each of the Rz is independently selected from the group consisting of H, COO($R_5$), CONH($R_5$), CON($R_5$)$_2$, CO($R_5$) and $R_5$, in which each $R_5$ is independently selected from $(C_1-C_4)$alkyl, halo$(C_1-C_4)$alkyl, aryl$(C_1-C_4)$alkyl and heteroaryl$(C_1-C_4)$alkyl, in which each $R_5$ is optionally substituted with a substituent selected from OH, halogen, $(C_1-C_4)$alkyl, $(C_1-C_4)$alkoxy, aryl$(C_1-C_4)$alkyl, aryl, heteroaryl$(C_1-C_4)$alkyl and heteroaryl; or a pharmaceutically acceptable acid addition salt of such compound, wherein a heteroaryl is a monocyclic or polycyclic heteroaromatic substituent containing from 1 to 13 carbon atoms and from 1 to 4 heteroatoms selected from oxygen, sulphur, nitrogen and selenium, and heterocyclyl is a saturated or partially unsaturated cyclic hydrocarbon based substituent containing from 1 to 13 carbon atoms and from 1 to 4 heteroatoms selected from oxygen, sulphur, nitrogen and selenium;

with the proviso that, when $R_1$ is (E)CH=CH—C(CH$_3$)$_3$, $R_2$ is methyl and $R_3$ is H, then m is other than 0.

26. A compound of formula (IV)

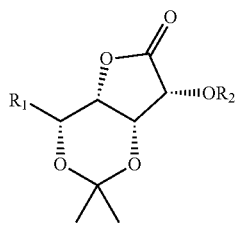

(IV)

wherein
$R_2$ is methyl and
$R_1$ is -(E)-CH=CH—C$_5$H$_9$.

27. A compound of formula (V)

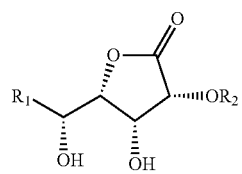

(V)

wherein
$R_2$ is methyl and
$R_1$ is -(E)-CH=CH—C$_5$H$_9$.

28. A compound of formula (VI)

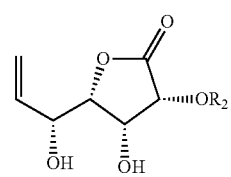

(VI)

wherein $R_2$ is methyl.

29. The compound according to claim 1 where in Formula I, the carbon atom attached to the exocyclic amine is in the S configuration.

* * * * *